(12) United States Patent
Kendler et al.

(10) Patent No.: US 8,011,224 B2
(45) Date of Patent: Sep. 6, 2011

(54) METHOD AND DEVICE FOR DETECTING AND IDENTIFYING CHEMICAL AGENTS

(75) Inventors: Shai Kendler, Rishon-LeZion (IL); Adi Zifman, Kfar-Saba (IL); Netzah Gratziany, Moshav Beit Hanan (IL); Amnon Sharon, Bitzaron (IL); Gad Frishman, Givataim (IL)

(73) Assignee: Israel Institute for Biological Research, Nes Ziona (IL)

( * ) Notice: Subject to any disclaimer, the term of this patent is extended or adjusted under 35 U.S.C. 154(b) by 230 days.

(21) Appl. No.: 11/631,524

(22) PCT Filed: Jun. 1, 2005

(86) PCT No.: PCT/IL2005/000574
§ 371 (c)(1),
(2), (4) Date: Jan. 4, 2007

(87) PCT Pub. No.: WO2006/003646
PCT Pub. Date: Jan. 12, 2006

(65) Prior Publication Data
US 2008/0105036 A1 May 8, 2008

(30) Foreign Application Priority Data
Jul. 7, 2004 (IL) .......................... 162906

(51) Int. Cl.
*B01D 53/02* (2006.01)
*G01N 1/40* (2006.01)
*G01N 30/62* (2006.01)

(52) U.S. Cl. ...... 73/31.05; 73/23.4; 73/23.41; 73/23.42; 73/31.01; 95/82; 95/148; 96/106

(58) Field of Classification Search ................ 95/87, 89, 95/148, 82; 96/105, 106; 73/23.4, 23.41, 73/23.42, 31.01, 31.02, 31.05; 422/88, 89
See application file for complete search history.

(56) References Cited

U.S. PATENT DOCUMENTS
3,159,996 A 12/1964 Norem
(Continued)

FOREIGN PATENT DOCUMENTS
EP 1763664 3/2007
(Continued)

OTHER PUBLICATIONS

Badman et al. "Miniature Mass Analyzers", Journal of Mass Spectrometry, 35:659-671, 2000.
(Continued)

*Primary Examiner* — Robert A Clemente

(57) ABSTRACT

A feeding device for enriching and feeding a fluid sample into a chemical detector, the feeding device comprises (a) a sorbent element having a sorbent material for sorbing at least one target chemical present in the fluid sample; (b) a desorbing mechanism for generating conditions for the sorbent material to desorb the at least one target chemical out of the sorbent material, thereby to provide an enriched fluid sample; and (c) a loose connector, for providing a loose connection between the feeding device and the chemical detector, such that when the sorbent material desorbs the at least one target chemical, the chemical detector is fed by the enriched fluid sample, and when the sorbent material sorbs the at least one target chemical, the chemical detector is fed by environmental fluids.

16 Claims, 14 Drawing Sheets

U.S. PATENT DOCUMENTS

| | | | |
|---|---|---|---|
| 4,180,389 | A | 12/1979 | Paul |
| 4,420,679 | A | 12/1983 | Howe |
| 5,005,399 | A | 4/1991 | Holtzclaw et al. |
| 5,014,541 | A | 5/1991 | Sides et al. |
| 5,123,276 | A | 6/1992 | Hartman et al. |
| 5,611,846 | A | 3/1997 | Overton et al. |
| 5,665,314 | A | 9/1997 | Berger et al. |
| 5,782,964 | A | 7/1998 | Mustacich |
| 5,830,353 | A | 11/1998 | Henderson |
| 6,093,921 | A | 7/2000 | Gaisford et al. |
| 6,148,657 | A * | 11/2000 | Satoh et al. ............ 73/23.35 |
| 6,209,386 | B1 | 4/2001 | Mustacich et al. |
| 6,217,829 | B1 | 4/2001 | Mustacich et al. |
| 6,223,584 | B1 | 5/2001 | Mustacich et al. |
| 6,341,520 | B1 * | 1/2002 | Satoh et al. ............ 73/23.35 |
| 6,423,120 | B1 * | 7/2002 | Nickerson et al. ............ 95/87 |
| 6,455,003 | B1 | 9/2002 | Anvia et al. |
| 6,477,905 | B1 | 11/2002 | Mitra |
| 6,530,260 | B1 | 3/2003 | Mustacich et al. |
| 6,550,961 | B1 * | 4/2003 | Ueda ............ 374/44 |
| 6,652,625 | B1 * | 11/2003 | Tipler et al. ............ 95/82 |
| 6,656,738 | B1 * | 12/2003 | Vogel et al. ............ 436/161 |
| 6,814,785 | B2 * | 11/2004 | Tipler et al. ............ 96/105 |
| 6,974,495 | B2 * | 12/2005 | Tipler et al. ............ 96/105 |
| 7,311,757 | B2 * | 12/2007 | Tipler et al. ............ 95/82 |
| 2002/0024672 | A1 * | 2/2002 | Shibamoto ............ 356/417 |

FOREIGN PATENT DOCUMENTS

| | | |
|---|---|---|
| WO | WO 03/045534 | 5/2003 |
| WO | WO 2006/003646 | 1/2006 |

OTHER PUBLICATIONS

Frishman et al. "Fast GC-PFPD System for Field Analysis of Chemical Warfare Agents", Field Analytical Chemistry and Technology, 4(4):170-194, 2000.

Grail et al. "Column Performance and Stability for High-Speed Vacuum-Outlet GC of Volatile Organic Compounds Using Atmospheric Pressure Air as Carrier Gas", Anal. Chem, 71(22):5199-5205, 1999.

Sanchez et al. "On-Line Multibed Sorption Trap and Injector for the GC Analysis of Organic Vapors in Large-Volume Air Samples", Analytical Chemistry, 75(4):978-985, 2003.

Syage et al. "A Man-Portable, Photoionization Time-of-Flight Mass Spectrometer", Field Analytical Chemistry and Technology, 4(4):204-215, 2000.

International Search Report and the Written Opinion Dated Dec. 2, 2005 From the International Searching Authority Re.: Application No. PCT/IL2005/000574.

International Preliminary Report on Patentability Dated Jan. 18, 2007 From the International Bureau of WIPO Re.: Application No. PCT/IL2005/000574.

Office Action Dated Mar. 18, 2009 From the Israeli Patent Office Re.: Application No. 162906 and Its Translation Into English.

Office Action Dated Feb. 6, 2008 From the Israeli Patent Office Re.: Application No. 162906.

Office Action Dated Feb. 22, 2011 From the Israeli Patent Office Re.: Application No. 162906 and Its Translation Into English.

Grall et al. "Column Performance and Stability for High-Speed Vacuum-Outlet GC of Volatile Organic Compounds Using Atmospheric Pressure Air as Carrier Gas", Anal. Chem, 71(22):5199-5205, 1999.

* cited by examiner

METHOD AND DEVICE FOR DETECTING AND IDENTIFYING CHEMICAL AGENTS

RELATED APPLICATIONS

This Application is a National Phase of PCT Patent Application No. PCT/IL2005/000574 having International Filing Date of Jun. 1, 2005, which claims the benefit of Israel Patent Application No. 162906 filed on Jul. 7, 2004. The contents of the above Applications are all incorporated herein by reference.

FIELD AND BACKGROUND OF THE INVENTION

The present invention relates to detection and identification of chemicals and, more particularly, to a method, device and system for detecting and identifying low levels of chemical agents, warfare chemical agents in particular.

Detection and identification of chemical agents include, inter alia, the use of surface acoustic wave detectors, ion mobility spectrometers, flame photometric detectors and the like.

In surface acoustic wave detectors, the target chemicals are absorbed or adsorbed onto a specific coating of a piezoelectric substrate, to thereby vary its mass. The mass change affects the resonance frequency of the piezoelectric substrate which is measured using an appropriate electronic circuitry.

In ion mobility spectrometer, a gaseous sample is ionized in an ionization region within the spectrometer, e.g., using a radioactive source, and accelerated over a short distance to a detector. The gaseous sample is analyzed by measuring a characteristic time-of-flight of the negative and positive ions from the ionization region to the detector.

In flame photometric detectors (FPDs) a gaseous sample is introduced to a hydrogen rich flame and electrons in the outer shell of atoms obtained from the target chemicals are excited to higher energy states. When an excited electron returns to its ground state, energy is emitted in the form of light by which the presence of target chemicals is confirmed. The wavelength of the emitted light depends on the target chemical, whereas its intensity depends on the chemical's concentration.

The above techniques have limited sensitivity and selectivity, in particular in environments, such as battlefield or industrial environments, in which the detection and identification of chemical agents must be performed under less than optimal conditions. It is recognized that when the chemical agents are extremely toxic, for example in the case of chemical warfare agents, very low levels thereof must be detected rapidly and efficiently.

Reliable on-site, real time, detection of trace levels of chemical agents is of utmost importance in particular for highly toxic chemical agents where lack of sensitive and accurate identification can dramatically increase the number of casualties. To prevent injury resulting from exposure to toxic chemicals, the presence of toxic chemicals must be detected while their concentrations are below toxic levels. Accordingly, to detect highly toxic chemicals, devices capable of detecting and identifying low concentrations within a short period of time are needed. For example, the toxic threshold level values of O-Ethyl S-2-diisopropylaminoethyl methyl phosphonothiolate (VX) and O-isopropyl methyl phosphonofluoridate (sarin—GB) are, respectively, $1 \times 10^{-5}$ and $1 \times 10^{-4}$ µg/L [Department of Defense (DOD) ammunition and explosive safety and standards, 1992, assistant secretary of defense (production and logistics, October 1992, DOD 6055.9 STD]. These values are about two orders of magnitude lower than the toxic threshold level value of common pesticides, e.g., parathion [Niosh pocket guide to chemical hazards, www.cdc.gov/niosh/npg].

Portable detectors based on the above techniques are known (to this end see, e.g., Brletich N. R., Waters M. J., Bowen G. W., Tracy M. F., "Worldwide Chemical Detection Equipment Handbook," CBIAC, October 1995). However, when these devices are used in the field, their performance is often compromised, e.g., due to lack of supportive periphery. For example, detection limits of conventional hand-held chemical warfare agent detectors are from about $10^{-2}$ to about $10^{-1}$ µg/L [N. R. Brletich, M. J. Waters, G. W. Bowen and M. F. Tracy, "Worldwide Chemical Detection Equipment Handbook," CBIAC, October 1995], which is about two or three orders of magnitude higher than the toxic threshold level values of VX and sarin as well as other hazardous chemical agents.

Several laboratory devices were adapted for field application in the past [U.S. Pat. No. 5,611,846; H. L. Meuzelaar, J. P. Dworzanski, N. S. Arnold, W. H. McClennen and D. J. Wager, Field Anal. Chem. Tech., 4, 3 (2000); E. R. Badman and R. G. Cooks, J. Mass Spectrom., 35, 659 (2000); and J. A. Syage, M. A. Hanning-Lee and K. A. Hanold, Field Anal. Chem. Tech., 4, 204 (2000)].

These devices, however, are expensive and are not sufficiently robust for massive deployment in the field.

Furthermore, due the continuously increasing demands of the modern battlefield environment, the required detection sensitivity of hand-held detectors is likely to be significantly increased, far beyond the capabilities of conventional devices.

One method of improving conventional chemical warfare agent detectors is disclosed in U.S. Pat. No. 6,455,003. In this method, the sample is enriched, prior to detection by the detector, by collecting a portion of the target chemicals within a sorbent element. Subsequently, the target chemicals are thermally desorbed into the detector [J. M. Sanchez and R. D. Sacks, Anal. Chem., 75, 978 (2003)].

An injection assembly for short path thermal desorption apparatus is disclosed in U.S. Pat. No. 5,123,276. The injection assembly includes a desorption tube for collecting and storing the sample compound to be analyzed and a needle injector for passing the desorbed sample component to a gas chromatograph unit for identification and quantification of the sample component.

U.S. Pat. No. 6,477,905 discloses a device for measurement of organic compound contaminants in a fluid sample stream. The device includes adsorbent trap for adsorbing the organic compound contaminants, while venting out permanent gases. The adsorbent trap is capable of rapid heating and cooling for rapidly desorbing the organic compound contaminants therefrom. Once desorbed, the contaminants enter a detector for measurement and analysis.

Sampling units are commercially available from CMS Research Corporation, Birmingham, Ala. or CDS Analytical, Inc., Oxford, Pa. These units are capable of detecting or improving detection capability of existing chemical agent detectors [see, e.g., U.S. Pat. Nos. 4,180,389 and 5,014,541]. Yet, their operation requires pure compressed gases and other consumable items, which makes massive deployment in the field problematic.

Additional prior art of interest is Amirav et al. [A. Amirav and G. Frishman, Field Anal. Chem. Tech., 4, 170 (2000)] in which low levels of chemical warfare agent simulants (stable, non toxic organo phosphor/sulfur compounds) were separated with a fast Gas Chromatograph (GC) system, equipped with a Pulsed Flame Photometric Detector (PFPD).

The use of air as a carrier gas for gas chromatographic separations has been investigated [A. J. Grall and R. D. Sacks, Anal. Chem., 71, 5199 (1999)] by separating stable volatile organic molecules with a laboratory gas chromatograph, using air as a carrier gas.

U.S. Pat. No. 6,223,584 discloses a system having an analyzing gas chromatographic unit, an in-line pre-concentrator assembly, an adsorbent material and a transfer line unit. When a trap housing present in the pre-concentrator assembly is displaced from the transfer line unit, the medium surrounding the trap housing is forced inside of the trap housing and vapor constituents are adsorbed on the adsorbent material. When the trap housing is moved with the transfer line unit, the adsorbent material is heated to release the vapor constituents from the adsorbent material.

Still additional prior art of relevance include U.S. Pat. Nos. 3,159,996, 4,420,679, 5,014,541, 5,005,399, 5,782,964, 5,665,314, 5,830,353, 6,093,921, 6,209,386, 6,217,829 and 6,530,260, the contents of which are hereby incorporated by reference.

However, the above attempts present several difficulties and limitations, especially in conjunction with portable detectors.

First, as the sensitivity enhancement is achieved by sorbing the target chemicals from a large volume of air and desobing it into a smaller volume, a skilled artisan would appreciate that portable detectors should, in principle, pump large volumes of air (typically about 0.5-5 L/min). Therefore, in order to obtain a gain factor of, say, 100, the sample volume should be about 50-500 L. Sampling such large volumes of air is both time consuming and requires large amount of power.

Second, in known sample enrichment methods, the chemical warfare agents, like any other semi volatile organic compound, desorb slowly from the sorbent material. Slow desorbtion dilutes the sample and reduces the sensitivity and selectivity of the detection process. In laboratory devices the slow desorbtion problem can be resolved by utilizing cryofocusing prior to detection. In portable devices, in contrast, cryofocusing is not applicable.

Third, in known sample enrichment methods the chemical warfare agents which are thermo-labile target chemicals may decompose during the thermal desorbtion.

Forth, it is difficult to operate prior art systems employing sample enrichment units in open field, because in such conditions the sorbent material tends to degrade, hence to decrease the efficiency of the detection and identification process.

There is thus a widely recognized need for, and it would be highly advantageous to have a method, device and system for detecting and identifying chemical agents, devoid of the above limitations.

SUMMARY OF THE INVENTION

According to one aspect of the present invention there is provided a feeding device for enriching and feeding a fluid sample into a chemical detector, the feeding device comprising: (a) a sorbent element having a sorbent material for sorbing at least one target chemical present in the fluid sample; (b) a desorbing mechanism for generating conditions for the sorbent material to desorb the at least one target chemical out of the sorbent material, thereby to provide an enriched fluid sample; and (c) a loose connector, for providing a loose connection between the feeding device and the chemical detector, such that when the sorbent material desorbs the at least one target chemical, the chemical detector is fed by the enriched fluid sample, and when the sorbent material sorbs the at least one target chemical, the chemical detector is fed by environmental fluids.

According to another aspect of the present invention there is provided a system for detecting and identifying chemicals, the system comprising: (a) a chemical detector, capable of detecting at least one target chemical having a predetermined concentration; (b) a feeding device for enriching and feeding a fluid sample into the chemical detector, the feeding device comprising: (i) a sorbent element having a sorbent material for sorbing the at least one target chemical; (ii) a desorbing mechanism for generating conditions for the sorbent material to desorb the at least one target chemical out of the sorbent material, thereby to provide an enriched fluid sample; and (iii) a loose connector, for providing a loose connection between the feeding device and the chemical detector, such that when the sorbent material desorbs the at least one target chemical, the chemical detector is fed by the enriched fluid sample, and when the sorbent material sorbs the at least one target chemical, the chemical detector is fed by environmental fluids.

According to yet another aspect of the present invention there is provided a feeding device for enriching and feeding a fluid sample into a chemical detector, the feeding device being loosely connectable to the chemical detector and comprising a sorbent material for sorbing and desorbing at least one target chemical present in the fluid sample, such that when the sorbent material desorbs the at least one target chemical, a detection sensitivity of the chemical detector is increased by a factor of at least 10.

According to further features in preferred embodiments of the invention described below, the feeding device further comprises at least one pumping device for transferring environmental fluids into the sorbent element when the sorbent material sorbs the at least one target chemical, and transferring the enriched fluid sample into the chemical detector when the sorbent material desorbs the at least one target chemical.

According to still further features in the described preferred embodiments the feeding device further comprises a multi-way valve for controlling flow direction of the enriched fluid sample and the environmental fluids.

According to still further features in the described preferred embodiments the feeding device further comprises electronic circuitry for actuating the multi-way valve.

According to still further features in the described preferred embodiments the multi-way valve is characterized by at least two operational phases, whereby in a first operational phase of the at least two operational phases fluids flow through the sorbent material in one direction and in a second operational phase of the at least two operational phases fluids flow through the sorbent material in an opposite direction.

According to still further features in the described preferred embodiments the electronic circuitry is designed and configured such that when the sorbent material sorbs the at least one target chemical, the multi-way valve is switched to the first operational phase, and when the sorbent material desorbs the at least one target chemical, the multi-way valve is switched to the second operational phase.

According to still further features in the described preferred embodiments the multi-way valve is a six-way valve.

According to still another aspect of the present invention there is provided a method of improving detection sensitivity of a chemical detector, the method comprising: (a) passing a fluid sample potentially having at least one target chemical through a sorbent material, while allowing environmental fluids to enter the chemical detector, thereby sorbing the at least one target chemical in the sorbent material; (b) generating conditions for the sorbent material to desorb the at least one target chemical out of the sorbent material, thereby providing an enriched fluid sample; and (c) feeding the chemical detector with the enriched fluid sample; thereby improving the detection sensitivity of the chemical detector.

According to further features in preferred embodiments of the invention described below, the method further comprises separating the enriched sample using a separating column.

According to still further features in the described preferred embodiments the enriched fluid sample is fed to a sensing element of the chemical detector.

According to still further features in the described preferred embodiments the environmental fluids are allowed to enter the sensing element at all times.

According to still further features in the described preferred embodiments the generation of conditions for the sorbent material to desorb the at least one target chemical is effected by a procedure selected from the group consisting of a thermal desorption, an electrical desorption, a depressurized desorption, a laser desorption and a laser induced thermal desorption.

According to still further features in the described preferred embodiments the generation of conditions for the sorbent material to desorb the at least one target chemical is by heating using a heating element.

According to still further features in the described preferred embodiments the heating is at a predetermined heating rate, the predetermined heating rate being sufficiently fast so as to prevent or minimize decomposing of the at least one target chemical by the heating.

According to still further features in the described preferred embodiments the heating is to a predetermined temperature, the predetermined temperature being sufficiently below a decomposing temperature of the at least one target chemical, so as to prevent or minimize decomposing of the at least one target chemical by the heating.

According to still further features in the described preferred embodiments the method further comprises controlling a heating power of the heating element, substantially in real time.

According to still further features in the described preferred embodiments steps (a)-(c) are performed such that when the chemical detector is fed by the enriched fluid sample, a detection sensitivity of the chemical detector is increased by a factor of at least 10, more preferably at least 30, most preferably at least 50.

According to one aspect of the present invention there is provided an air purification system having an inlet and an outlet, the air purification system comprising: (a) a chemical detector, positioned between the inlet and the outlet of the air purification system and capable of detecting at least one target chemical having a predetermined concentration; (b) a feeding device, loosely connected to the chemical detector, for enriching and feeding a fluid sample into the chemical detector, the feeding device comprises: (i) a sorbent element having a sorbent material for sorbing the at least one target chemical; (ii) a desorbing mechanism for generating conditions for the sorbent material to desorb the at least one target chemical of the sorbent material, thereby to provide an enriched fluid sample; and (iii) a loose connector, for providing a loose connection between the feeding device and the chemical detector, such that when the sorbent material desorbs the at least one target chemical, the chemical detector is fed by the enriched fluid sample, and when the sorbent material sorbs the at least one target chemical, the chemical detector is fed by environmental fluids; (d) at least one purifying element, positioned between the inlet and the outlet of the air purification system, for purifying at least a portion of air entering the inlet, thereby providing purified air; and (e) an airflow mechanism for generating flow of the purified air through the outlet.

According to further features in preferred embodiments of the invention described below, the chemical detector is capable of generating a signal indicative of the presence of the at least one target chemical.

According to still further features in the described preferred embodiments the at least one purifying element comprises a sorbent material.

According to still further features in the described preferred embodiments the at least one purifying element comprises a radiation generator.

According to still further features in the described preferred embodiments the radiation generator is an ultraviolet generator.

According to still further features in the described preferred embodiments the at least one purifying element comprises a particulate immobilizing medium.

According to still further features in the described preferred embodiments the feeding device may further comprise a separating column connected to the loose connector for separating the enriched sample.

According to still further features in the described preferred embodiments the separating column is a separating capillary column.

According to still further features in the described preferred embodiments the separating capillary column is an open tubular column coated with an inert film.

According to still further features in the described preferred embodiments the separating capillary column is an open tubular column having an internal surface coated with a porous layer.

According to still further features in the described preferred embodiments the separating column is a packed column.

According to still further features in the described preferred embodiments the loose connector is designed and constructed to allow transfer of the enriched fluid sample to a sensing element of the chemical detector.

According to still further features in the described preferred embodiments the loose connector is designed and constructed so as to allow the environmental fluids to bypass the loose connector and enter the sensing element at all times.

According to still further features in the described preferred embodiments the desorbing mechanism is selected from the group consisting of a thermal desorbing mechanism, an electrical desorbing mechanism, a depressurized desorbing mechanism, a laser desorbing mechanism and a laser induced thermal desorbing mechanism.

According to still further features in the described preferred embodiments the desorbing mechanism comprises a heating element.

According to still further features in the described preferred embodiments the heating is characterized by a heating rate of at least 500 degrees centigrade per minute, more preferably at least 1000 degrees centigrade per minute, most preferably at least 1200 degrees centigrade per minute.

According to still further features in the described preferred embodiments the sorbent material is substantially dry.

According to still further features in the described preferred embodiments a water vapor breakthrough volume of the sorbent material is smaller than a water vapor breakthrough volume of the at least one target chemical by at least two orders of magnitude.

According to still further features in the described preferred embodiments the desorbing mechanism is configured to heat the sorbent material at a predetermined heating rate, the predetermined heating rate being sufficiently fast so as to prevent or minimize decomposition of the at least one target chemical.

According to still further features in the described preferred embodiments the desorbing mechanism is configured to heat the sorbent material to a predetermined temperature, the predetermined temperature being sufficiently below a decomposing temperature of the at least one target chemical.

According to still further features in the described preferred embodiments the desorbing mechanism further comprises a heating control element for controlling a heating power of the heating element.

According to still further features in the described preferred embodiments the heating control element is supplemented with an algorithm for optimizing the heating power, substantially in real time.

According to still further features in the described preferred embodiments the sorbent material, the desorbing mechanism and the loose connector are designed and constructed such that when the chemical detector is fed by the enriched fluid sample, a detection sensitivity of the chemical detector is increased by a factor of at least 10, more preferably at least 30, most preferably at least 50.

According to still further features in the described preferred embodiments the sorbent material is absorbent material.

According to still further features in the described preferred embodiments the sorbent material is adsorbent material.

According to still further features in the described preferred embodiments the sorbent material is selected from the group consisting of porous inert hydrophobic polymer, activated non-synthetic carbon, activated synthetic carbon, silica, alumina and combinations thereof.

According to still further features in the described preferred embodiments the sorbent material comprises a solid support.

According to still further features in the described preferred embodiments the solid support comprises glass beads.

According to still further features in the described preferred embodiments the solid support is a porous solid support.

According to still further features in the described preferred embodiments the porous solid support comprises a cross linked porous polymer.

According to still further features in the described preferred embodiments the solid support is coated with an inert film.

According to still further features in the described preferred embodiments the inert film comprises a material selected from the group consisting of polydimethylsiloxane gum and polydiphenil/polydimethylsiloxane gum.

According to still further features in the described preferred embodiments the at least one target chemical is selected from the group consisting of a chemical warfare agent, a toxic industrial chemical, an explosive and a narcotic chemical.

According to still further features in the described preferred embodiments the at least one target chemical comprises a sulfur, phosphate and/or nitrogen bearing compound.

According to still further features in the described preferred embodiments the sulfur bearing compound is selected from the group consisting of methyl parathion, fenitrothion and fensulfothion.

According to still further features in the described preferred embodiments the chemical warfare agent is selected from the group consisting of a nerve blocking agent, a blister inducing agent, a choke inducing agent, a vomiting inducing agent and a blood destructing agent.

According to still further features in the described preferred embodiments the nerve blocking agent is selected from the group consisting of tabun, methylphosphonothioic acid, sarin and soman.

According to still further features in the described preferred embodiments the blister inducing agent is selected from the group consisting of sulphur mustard, nitrogen mustard, distilled mustard, mustard lewisite, lewisite, phosgene oximine, ethyldichloroarsine and methyldichloroarsine.

According to still further features in the described preferred embodiments the choke inducing agent is selected from the group consisting of phosgene, diphosgene, chlorine and chloropicrin.

According to still further features in the described preferred embodiments the vomiting inducing agent is selected from the group consisting of diphenyl-dichloroarsine, adamsite and diphenylcyanoarsine.

According to still further features in the described preferred embodiments the blood destructing agent is selected from the group consisting of hydrogen cyanide, cyanogen chloride and arsine.

According to still further features in the described preferred embodiments the chemical detector is a portable chemical detector.

According to still further features in the described preferred embodiments the gas chromatography detector is selected from the group consisting of a flame photometric detector, a pulse flame photometric detector, a flame ionization detector, an electrolyzer-powered flame ionization detector, an electron capture detector, a pulse discharge electron capture detector, a flame thermocouple detector, a radioactivity detector, an radiofrequency discharge detector, a surface acoustic wave detector, an absolute mass detector, a surface potential detector, a surface acoustic wave detector, an ion mobility spectrometer and a katharometer.

According to yet an additional aspect of the present invention there is provided a method of desorbing chemicals from a sorbent material, the method comprising, (a) continuously measuring a temperature of the sorbent material; (b) applying a predetermined power to a heating element so as to increase the temperature to a predetermined temperature threshold; and (c) reducing the predetermined power as a function of a difference between the temperature to the temperature threshold; thereby desorbing chemicals from a sorbent material.

According to further features in preferred embodiments of the invention described below, the function of the difference comprises at least one exponential function.

According to still further features in the described preferred embodiments the function of the difference comprises a bias parameter.

According to still further features in the described preferred embodiments the function of the difference comprises a damping parameter.

According to still further features in the described preferred embodiments the function of the difference equals zero when the temperature equals a sum of the bias parameter and the temperature threshold.

According to still further features in the described preferred embodiments step (a) is executed by a device selected from the group consisting of a thermocouple-based temperature measuring device, a resistance-based temperature measuring device and a radiation-based temperature measuring device.

According to still further features in the described preferred embodiments the temperature threshold is lower than a decomposition temperature of the chemicals, so as to prevent or minimize decomposing of the at least one target chemical by the heating.

The present invention successfully addresses the shortcomings of the presently known configurations by providing a method, feeding device and system for chemical detection, having properties far exceeding prior art systems.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

(FIG. 8a) and 150° C. (FIG. 8b), obtained in the first operational phase of the feeding device, according to a preferred embodiment of the present invention;

FIG. 12a shows the effect of flow rate on peaks width for TBP, according to a preferred embodiment of the present invention;

FIGS. 12b-c show the effect of flow rate on peaks amplitude (FIG. 12b) and area (FIG. 12c), for TBP and VX.

DESCRIPTION OF THE PREFERRED EMBODIMENTS

Figure 1A:
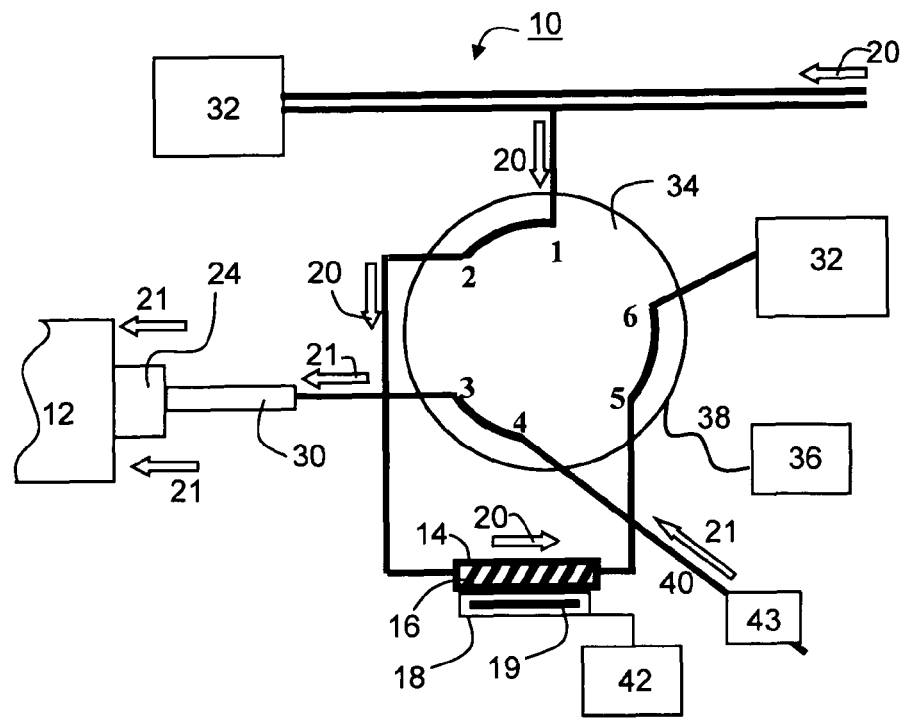
FIG. 1a is a schematic illustration of a feeding device for improving chemical detection sensitivity, in a first operational phase of the device in which target chemicals are absorbed in a sorbent material, according to a preferred embodiment of the present invention.

The present invention is of a method of and a feeding device for improving chemical detection sensitivity, which can be used to provide an enriched environment to chemical detectors in many civil and military applications.

Specifically, the present invention can be used to detect and identify low levels of many chemical agents, including, without limitation, chemical warfare agents, toxic industrial chemical agents, explosives and narcotic chemical agents.

The present invention is further of chemical detection and air purification systems incorporating the feeding device.

The principles and operation of a method, device and system for detecting and/or identifying chemical agents according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The feeding device of the present invention improves the detection sensitivity of conventional chemical detectors by providing a new, enriched, environment in which the concentration of target chemicals is substantially larger than the environmental concentration. As further demonstrated in the Example section that follows, the enhanced concentration allows conventional chemical detectors to efficiently detect and identify the target chemicals even when the environmental concentration is far below the characteristic threshold of detection. The enriching of the environment is achieved by collecting the target chemicals from a large volume of fluid (e.g., air) and releasing them in a smaller fluid volume.

The collection of target chemicals is preferably done by allowing the fluid to flow through a collection zone for a predetermined time period. For a given cross sectional area of the collection zone, the effective volume of fluid from which the target chemicals are collected linearly increases with the velocity of the fluid and the time period. Thus, for high velocities of fluid and/or larger periods of collection time, large effective volumes of fluids can be achieved and a substantially large amount of target chemicals can be accumulated in the collection zone. The collected target chemicals are then released in the immediate environment of the chemical detector, hence providing an enriched environment thereto.

The feeding device of the present invention can be used as an add-on device for conventional chemical detectors. Thus, according to a preferred embodiment of the present invention the feeding device can be attached to an inlet member of the chemical detector in use, e.g., using a suitable connector which is designed specific to the inlet member. The connection between the feeding device of the present invention and the respective chemical detector can be made either permanent or temporal, depending on the application for which the feeding device and the chemical detector are used. For example, in military application, such as a battle field, where the connection is typically made by the end user, the feeding device of the present invention can be temporarily connected to the chemical detector, preferably by a fast, easy to operate, connector which requires minimal number or, more preferably, no tools for performing the connection (e.g., snap-on). In air purification systems, such as, for example, systems permanently installed in submarines or space shuttles in which a continuous detection of chemical is desired at all times, the connection between the feeding device of the present invention and the chemical detector can be made more permanent. In this embodiment, the feeding device can still be disconnected from the chemical detector, if desired, e.g., for maintenance, repair.

In any event, according to a preferred embodiment of the present invention the connection of the feeding device to the chemical detector is done such that during the time in which the target chemicals are collected, environmental fluids are still allowed to enter the chemical detector, substantially in an obstruction free manner. Such a connection is referred to herein as "loose connection."

The advantage of the loose connection between the feeding device of the present invention and chemical detector is three-fold.

First, the loose connection ensures a continuous operation of the chemical detector. Thus, unlike prior art systems in which during the accumulation of the target material no detection is being made, in the presently preferred embodiment of the invention the chemical detector is continuously fed. Thus, during the accumulation of the target chemical, the characteristic sensitivity of the chemical detector is restored, substantially as if the feeding device had not been connected thereto. Once the enriched environment is formed, the sensitivity of the chemical detector is significantly improved.

Second, the loose connection facilitates quality control of the detection. For example, the operation of the chemical detector can be verified by switching off the feeding device and monitoring the readings of the chemical detector in a known environment.

Third, as further detailed hereinunder, the loose connection allows enriching only a portion of the fluid arriving at the detector, substantially without obstructing additional flow into the detector, if such additional flow exists.

Referring now to the drawings, FIGS. 1*a*-*b* illustrate a feeding device, generally referred to herein as device 10. Device 10 can be used for enriching and feeding a fluid sample into a chemical detector 12. According to a preferred embodiment of the present invention, device 10 comprises a sorbent element 14 having a sorbent material 16 for sorbing one or more target chemical present in the fluid sample. Thus, sorbent element 14 serves as the aforementioned collection zone through which a sufficiently large volume of fluid flows, and in which target chemicals can be accumulated for a predetermined time period.

Sorbent material 16 can be any material capable of adsorbing or absorbing the target chemicals. Representative examples include, without limitation, porous inert hydrophobic polymer, activated non-synthetic carbon, activated synthetic carbon, silica, alumina and combinations thereof. Sorbent material 16 can also be in a form of a solid support (e.g., glass beads) and/or a porous solid support (e.g., a cross linked porous polymer) coated by an appropriate inert film, such as, but not limited to, a polydimethylsiloxane gum or a polydiphenil/polydimethylsiloxane gum.

Device 10 further comprises a desorbing mechanism 18 for generating conditions for sorbent material 16 to desorb the target chemical(s) out of sorbent material 16, as further detailed hereinunder.

In use, device 10 preferably has two operational phases. In a first operational phase, depicted in FIG. 1*a*, environmental fluids 20 are flown through sorbent material 16, such that a sufficient amount of the target chemical is accumulated in sorbent element 14. In a second operational phase, depicted in FIG. 1*b*, the direction of flow through sorbent element 14 is inverted, and at the same time, the target chemical is desorbed out of sorbent material 16. As will be understood by one of ordinary skill in the art, in this operational phase, when environmental fluids 20 flow through sorbent element 14, the level of the target chemical is increased and an enriched fluid sample 22 is provided. When enriched sample 22 is fed into chemical detector 12, the effective sensitivity of the detection process is increased, because the concentration of the target chemical entering detector 12 is substantially larger than the environmental concentration.

Any chemical detector is characterized by a detection threshold, typically specific to the type of the target chemical, below which the chemical detector is not sensitive to its presence. For example, AP2C™ is a commercially available chemical detector for chemical warfare agents manufactured by Proengin™ (France), for which, according to the manufacturer data, the detection thresholds are 0.01 μg/L for O-isopropyl methyl phosphonofluoridate (sarin-GB), 0.02 μg/L for O-Ethyl S-2-diisopropylaminoethyl methyl phosphonothiolate (VX) and 0.8 μg/L for distilled mustard (HD).

Figure 1B:
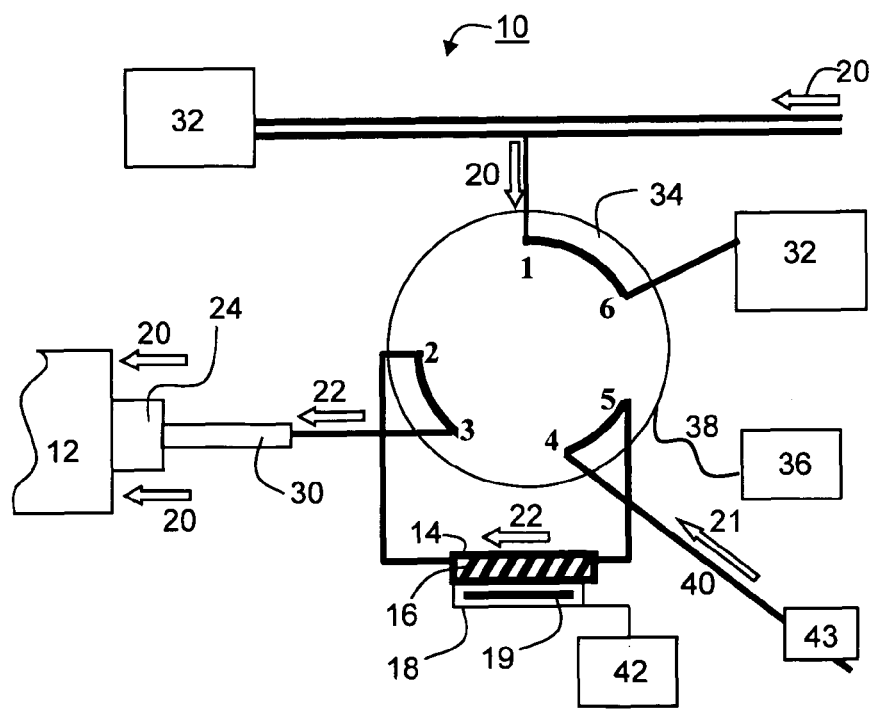
FIG. 1b is a schematic illustration of the feeding device of FIG. 1a in a second operational phase in which the target chemicals are desorbed out of the sorbent material, hence enrich a fluid sample passing therethrough, according to a preferred embodiment of the present invention.

According to a preferred embodiment of the present invention the duration of the first and second operational phases of device 10 is selected such that the amount of accumulated target chemical is sufficient to increase the concentration to a predetermined level which is above the characteristic threshold of detector 12, thereby to increase the detection sensitivity of detector 12. A typical duration of one cycle of operation of device 10 is from a few seconds to a few minutes. One of ordinary skill in the art would appreciate that longer durations are favored from stand point of detection and identification accuracy while short durations are favored from stand point of speed. A representative example for a duration of one cycle of device 10 is from about 4 minutes to about 5 minutes, out of which about 1-2 minutes are for collecting the target chemical and about 2-3 minutes are for providing enriched fluid sample 22 to detector 12.

As used herein the term "about" refers to ±25%.

Device 10 further comprises a loose connector 24, for providing the loose connection between device 10 and detector 12, mentioned hereinabove. The loose connection ensures that when sorbent material 16 desorbs the target chemical (see FIG. 1*b*), detector 12 is fed by enriched fluid sample 22, and when sorbent material 16 sorbs the target chemical (see FIG. 1*a*), detector 12 is fed by environmental fluids 20. During the collection of the target chemical, detector 12 preferably continues to operate substantially without obstruction.

According to a preferred embodiment of the present invention device 10 further comprises separating column 30, connected to loose connector 24. Column 30 serves for focusing different target chemicals present in environmental fluid 20 (FIG. 1*a*) or enriched fluid sample 22 (FIG. 1*b*), depending on the operational phase of device 10. Column 30 can be any known separating column, suitable for separation of the target chemicals. In one embodiment, column 30 is a capillary column which may be, for example, an open tubular column coated with an inert film. Representative examples of inert film include, without limitation, polydimethylsiloxane gum, polydiphenil/polydimethylsiloxane gum and the like. Column 30 may also be coated internally with a porous layer.

In another embodiment, column 30 is a packed column having a stable separating material. Typical dimensions of separating column 30 are from about 50 cm to about 3000 cm in length, and from about 0.1 mm to about 0.8 mm in internal diameter. Typical coating of column 30 comprises Crossbond-X diphenyl-Y dimethyl polysiloxane, where X preferably vary from about 1% to about 10% and Y preferably satisfies Y+X=100%.

The advantage of separating the target chemicals prior to their entrance into detector 12 is that column 30 facilitates focusing of the target chemicals once desorbed out of sorbent material 16 without the need of active cooling. This embodiment is particularly useful for semi volatile organic compounds. In this case dilution of enriched sample 22 due to slow desorption of the target chemical is substantially reduced or completely eliminated by separating column 30.

An additional advantage of column 30 is that different target chemicals, which typically have different delay periods within column 30, arrives at different times into detector 12 hence optimizing its identification capability. For example, in ion mobility spectrometers in which the identification capability is inherently limited by the ionic mobility, the use of column 30 significantly improves the identification capability far beyond the inherent limitation.

The transfer of environmental fluids 20 and enriched fluid sample 22 is preferably accomplished utilizing one or more pumping devices 32. Hence, in the first operational phase of device 10, during the sorption of the target chemical in sorbent material 16, pumping devices 32 facilitate transfer of environmental fluids 20 into sorbent element 14 (see FIG. 1*a*). In the second operational phase, during the desorption of the target chemical out of sorbent material 16, pumping devices 32 facilitate transfer of enriched fluid sample 22 into detector 12, e.g., via column 30.

To prevent or minimize degrading of sorbent material 16 and the coating of column 30, pumping devices 32 preferably generate a sufficient pressure difference to allow high flow-rates during desorption. The use of high flow-rates ensures that enriched fluid sample 22 enters detector 12 at sufficiently hence to decrease the low temperature of enriched fluid sample 22 [M. van Deursen, H. G. Janssen, J. Beens, G. Rutten and C. Cramers, J. Microcolumn Separations, 13:337 (2001); and A. B. Fialkov, A. Gordin and A. Amirav, J. Chromatog. A. 991, 217 (2003)]. This embodiment is particularly useful when device 10 is operated in air, which is known to degrade sorbent materials and column coatings at high temperatures [M. van Deursen, H. G. Janssen, J. Beens, G. Rutten and C. Cramers, J. Microcolumn Separations, 13:337 (2001); and A. B. Fialkov, A. Gordin and A. Amirav, J. Chromatog. A. 991, 217 (2003)].

The ability of device 10 to operate on air is an advantageous feature of the present embodiment, in particular in application in which device 10 serves as an add-on device for portable chemical detectors, e.g., in a chemical warfare battlefield. Hence, unlike prior art devices utilizing pure gas for transferring chemical warfare agent into the chemical detector, thereby requiring transportation of pure gas containers with the detector, the feeding device of the present invention is capable of operating on air without the need of any additional pure gas container to be transported therewith.

As stated, during the second operational phase of device 10, the direction of flow through sorbent element 14 is inverted relative to flow during the first phase. This can be done, for example, using a multi-way valve 34 which allows for controlling flow direction of enriched fluid sample and environmental fluids. Valve 34 preferably comprises a plurality of ports and capable of directing fluids from one port to the other by selectively opening and closing fluid communication between several ports. Multi-way valves are known in the art and are commercially available, for example from Valco Instruments Co. Inc. (VICI®), USA.

Device 10 preferably utilizes a suitable electronic circuitry 36 for actuating valve 34. Electronic circuitry can be either integrated with valve 34 or being provided as a separate unit, in which case a communication line 38 is preferably used for communicating between valve 34 and circuitry 36.

Shown in FIGS. 1*a-b* is a representative example in which six ports, designated by numerals 1-6, are employed. Thus, in this embodiment, valve 34 is a six-way valve. It is to be understood that it is not intended to limit the scope of the present invention to the use of a six-way valve and that other multi-way valves, having either a larger number or a smaller number of ports, are not excluded.

In the embodiment shown in FIGS. 1*a-b*, sorbent element 14 is connected between ports 2 and 5, pumping device 32 is connected to port 6, detector 12 is fed through port 3 and environmental fluids 20 are delivered into ports 1 and 4, e.g., via one or more vacuum channels 40. Open fluid communications between ports are shown in FIGS. 1a-b by solid arches.

Hence, in the first operational phase of device 10, (see FIG. 1a) fluid communications are opened between ports 1 and 2, ports 3 and 4 and ports 5 and 6. In this operational phase, pumping device 32 preferably applies an under pressure in port 4 where one end of sorbent element 14 is connected, and environmental fluids 20 entering port 1, flow through a respective conduit of valve 34 and exit through port 2 where the other end of sorbent element 14 is connected. Sorbent material 16 sorbs the target chemical present in environmental fluids 20 passing therethrough. Other environmental fluids 21 can be delivered via vacuum channel 40 to port 4 and transferred through the open fluid communication between ports 4 and 3 to thereby feed detector 12. Additionally, environmental fluids 20 are allowed to bypass loose connector 24 thereby to enter detector 12 to ensure its continuous operation. Optionally and preferably, fluids 21 pass through a filtering unit 43 prior to their entrance into detector 12, so as to remove one or more of the chemicals present therein. For example, in one embodiment all toxic chemical are removed by unit 43 such that fluids 21 are clean air.

Upon a proper signal generated by electronic circuitry 36, valve 34 is switched to the second operational phase. In this phase, (see FIG. 1b) fluid communications are opened between ports 2 and 3, ports 4 and 5 and ports 1 and 6. Fluids 21 are delivered via channel 40 into port 4, exit through port 5, pass through sorbent element 14 while being enriched therein, delivered into port 2 and exit through port 3 to thereby feed detector 12. According to a preferred embodiment of the present invention, in this operational phase fluids 20 can still bypass loose connector 24 as further detailed hereinabove.

Note that in the first phase, environmental fluids 20 pass through sorbent element 14 by flowing from port 2 to port 5, while in the second phase, environmental fluids 20 pass through sorbent element 14 by flowing from port 5 to port 2. Thus, by switching valve 34 between the first and second operational phases, the direction of flow through element 14 is inverted as required.

As stated, desorbing mechanism 18 generates conditions for sorbent material 16 to desorb the target in the second operational phase of device 10. Generally, desorbing mechanism 18 provides molecules of the target chemical with kinetic energy which is sufficient to escape the immediate region of molecules of material 16 where an attractive electrical potential is present. This can be done by any desorption procedure known in the art, including, without limitation, thermal desorption, electrical desorption, depressurized desorption, laser desorption, laser induced thermal desorption and the like.

According to a preferred embodiment of the present invention desorbing mechanism 18 comprises one or more heating elements 19, for heating element 14 thereby providing the necessary energy for the desorption process. Heating element can also be used for heating column 30 if desired. The heating power of element 14 is preferably selected such that the resulting heating rate (measured in units of thermal degrees per unit time) is sufficiently high, thereby enhancing the desorption rate of the target chemical from material 16. This embodiment is particularly useful in applications in which semi volatile organic compound are to be detected, e.g., when device 10 and detector 12 are used to detect and identify chemical warfare agents. In such applications, slow desorption may reduce the concentration of the target chemical in enriched fluid sample 22, hence also the sensitivity and selectivity of the detection process. The application of high heating rate, according to the presently preferred embodiment of the invention, facilitates the fast desorption and minimizes or eliminates dilution of enriched fluid sample 22.

A preferred heating rate of heating element 19 is about 500 degrees centigrade per minute or above, more preferably about 1000 degrees centigrade per minute or above, most preferably about 1200 degrees centigrade per minute or above.

It is recognized that extremely high temperatures may decompose the target chemicals, rendering them undetectable or unrecognizable by detector 12. For example, when the detection and identification of the target chemicals is based on transition between known energy levels of the molecules of the target chemicals, a decomposition of the molecules may results in false reading or inability of detector 12 to detect the target chemicals.

One such thermo-labile chemical is HD bis-(2-chloroethyl) sulfide. It is known that the changes in the HD vapor phase concentration are affected primarily by the HD loading on adsorbent material and temperature thereof. It has been demonstrated [Karwacki et al., "Effect of Temperature on the Desorption and Decomposition of HD from Activated Carbon," Storming Media LLC, 1998, A745873] that for each $25°$ C. increase in temperature, the vapor concentration of HD is changed by a factor of about 10. The decomposition of HD is primarily affected by the presence of co-adsorbed water and temperature. The major volatile products are 2-chloroethylvinylsulfide, 1,4-thioxane, and 1,4-dithiane, with the latter forming at elevated temperatures.

In addition to the temperature, the decomposition of the target chemical depends on the type of desorbing conditions and in particular on the humidity of sorbent material 16. Thus, according to a preferred embodiment of the present invention, the desorbing conditions are selected such that the decomposition of the target chemicals during the desorbtion phase is minimize or eliminated. There is are several measures which can be followed to achieve efficient desorption of the target chemical from material 16 substantially without decomposition.

For example the water content of sorbent material 16 may be reduced by keeping material 16 at relatively high temperatures, about $50°$ C. It is appreciated that this temperature is sufficient for providing a relatively dry sorbent material, yet without decomposing the target chemical. The hydrophobic property of sorbent material 16 can be quantified in terms of its water vapor breakthrough volume. According to a preferred embodiment of the present invention, water vapor breakthrough volume of material 16 is smaller than the water vapor breakthrough volume of the target chemical, by at least two orders of magnitude, more preferably by at least three orders of magnitude.

Desorbing mechanism 18 can also be configured to heat sorbent element 14 to a predetermined temperature in a predetermined rate such that for the particular type of material 16 and at the particular chemical conditions (e.g., humidity level) the decomposition of the target chemical is minimized or eliminated. According to a preferred embodiment of the present invention the predetermined temperature is sufficiently below the decomposing temperature of the target chemical.

The control of the heating rate and maximal temperature provided by mechanism 18 is preferably by a heating control element 42 communicating with mechanism 18 and preferably supplemented with one or more algorithms for optimizing the heating power of heating element 19.

It has been found by the present inventors that when the heating power of element 19 is a function of the temperature of sorbent material 16, a fast and accurate heating can be obtained. As demonstrated in the Examples section that follows, fast and accurate heating in this way an efficient desorption of the target chemical from sorbent material 16 can be achieved, substantially without decomposition.

Figure 2:
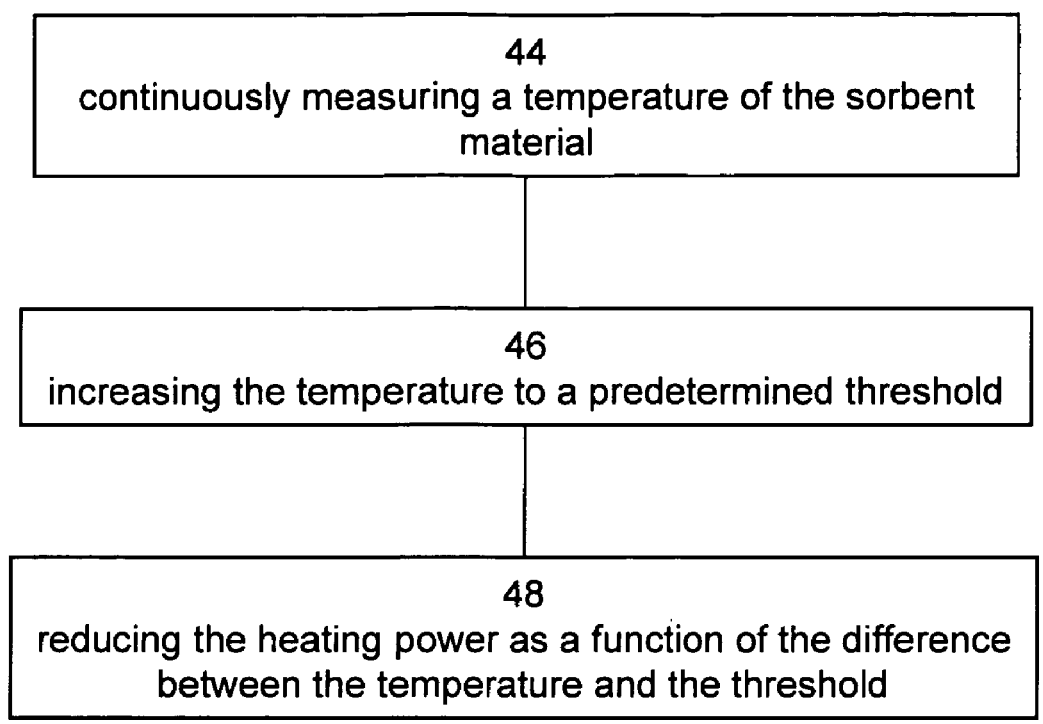
FIG. 2 is a flowchart diagram illustrating a method of desorbing target chemicals from a sorbent material, according to a preferred embodiment of the present invention.

Hence, according to a preferred embodiment of the present invention there is provided a method of desorbing the target chemicals from sorbent material 16. The method comprises the following method steps which are illustrated in the flowchart of FIG. 2.

In a first in a first step of the method, designated by block 44, a temperature, T, of sorbent material 16 is continuously measured, e.g., using a thermocouple or any other suitable device, and in a second step, designated by block 46, a predetermined power, $V_0$, is applied to heating element 19, so as to increase the temperature of sorbent material 16 to a predetermined temperature threshold, $T_{th}$. A third step of the method, designated in FIG. 2 by block 48, is preferably implemented once the temperature of sorbent material 16 equals $T_{th}$. In this step, the power $V_0$ is reduced as a function of the difference between the temperature, T, and the threshold, $T_{th}$. Optionally, once the temperature reaches setting value, designated $T_{set}$, the heating is ceased.

According to a preferred embodiment of the present invention the heating power applied to heating element 19 satisfies Equation 1, below:

$$V(T) = \begin{cases} V_0 & T < T_{th} \\ V_0(1 - \exp[(T - T_{tar} - B)/D]) & T_{th} \leq T < T_{set} \\ 0 & T \geq T_{set} \end{cases} \quad (EQ.\ 1)$$

where V(T) is the heating power at temperature T, B is a predetermined biasing parameter and D is a predetermined damping parameter. As can be understood from Equation 1, for low temperatures a constant heating power, $V_0$, is applied, while for higher temperatures the heating power decreases with the temperature, in accordance with the presently preferred embodiment of the invention. V(T) approaches the value of zero from above when $T=B+T_{th}$.

The above method can also be implemented for heating column 30 in which case the temperature of column 30 is continuously measured in the first step. In any event, the numerical values of the biasing parameter, B, and the damping parameter, D, are preferably determined according to the thermal response of the heated object (element 14 or column 30). Typically, the value of the biasing parameter, B, is, without limitation, from about 10° C. to about 30° C., the value of the damping parameter, D, is, without limitation, from about 15° C. to about 35° C. The maximal heating power, $V_0$, the threshold temperature $T_{th}$, and the setting temperature, $T_{set}$ appearing in Equation 1 typically depend on several variants such as, but not limited to, the resistance of the heating element, the thermal mass of the heated object and the type of target chemical. For example, for a resistance of about 5Ω, thermal mass of a few grams, and the chemicals described in the Examples section that follows, $V_0$ can vary between about 2 Volts and about 20 Volts, $T_{th}$ can vary between about 100° C. and about 300° C., and $T_{set}$ can vary between about 200° C. and about 400° C. Is to be understood that these values are not to be considered as limiting.

As demonstrated in the Example section that follows, Equation 1 can be used for achieving high heating efficiency. For example, for B=19° C. and D=25° C., a heating rate of about 1600° C./minute and a maximal temperature of about 200° C. can be obtained.

Figure 3A:
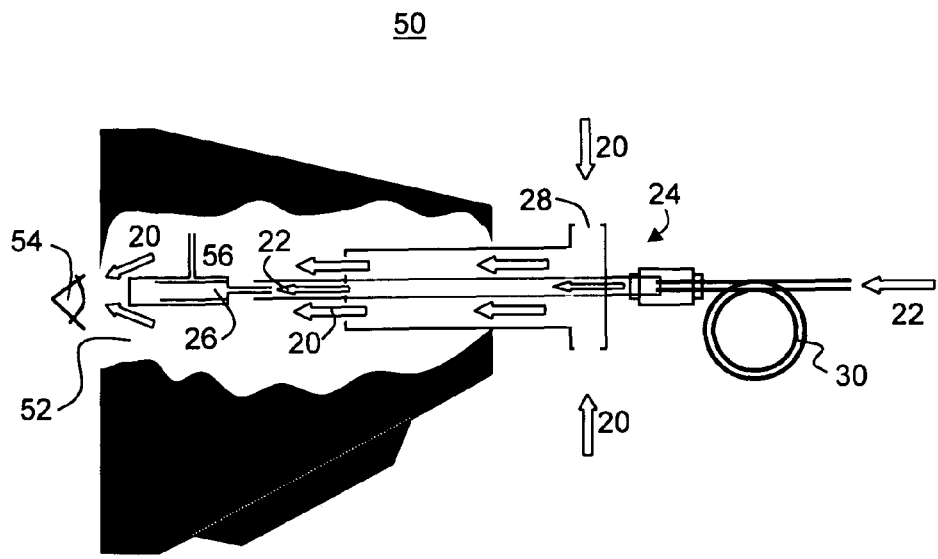
FIGS. 3a-c is a simplified illustration of a system for detecting and identifying chemicals, according to a preferred embodiment of the present invention.
Figure 3B:
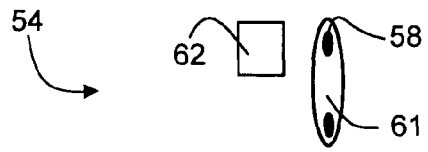
Figure 3C:
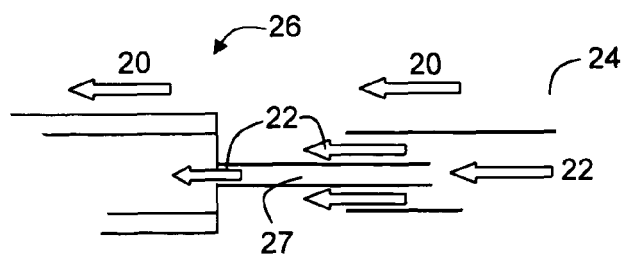

Reference is now made to FIGS. 3a-c, which are simplified illustrations of a system 50 for detecting and identifying chemicals. System 50 can be used in many applications, both as a portable system, e.g., for detection trace levels of chemical warfare agents in a battle field, and as fixed system which can be incorporated, e.g., in air purification systems of submarines, space shuttles and the like.

System 50 preferably comprises chemical detector 12, for detecting the target chemical and feeding device 10 for feeding detector 12 with enriched fluid sample 22 as further detailed hereinabove.

Detector 12 can be any known detector capable of identifying or detecting the target chemicals, e.g., a portable chemical detector. Representative examples include, without limitation, a flame photometric detector, a pulse flame photometric detector, a flame ionization detector, and electrolyzer-powered a flame ionization detector, an electron capture detector, a pulse discharge electron capture detector, a flame thermocouple detector, a radioactivity detector, an radiofrequency discharge detector, a surface acoustic wave detector, an absolute mass detector, a surface potential detector, a surface acoustic wave detector, an ion mobility spectrometer, a katharometer and the like.

Shown in FIGS. 3a-c is a flame photometric detector, having a combustion chamber 52, a sensing element 26 and electro-optic unit 54, where FIG. 3a illustrate system 50, and FIGS. 3b-c illustrate electro-optic unit 54 and element 26, respectively.

In this embodiment, the principle and operation of detector 12 is as follows. A flammable gas, e.g., hydrogen is fed into combustion chamber 52 through a separate inlet 56 and flam is ignited in the chamber. Fluids, which can be environmental fluids 20 as well as enriched fluid sample 22 (depending on the operational phase of device 10 as further detailed hereinabove) enter chamber 52 and being combusted in the flame. The combustion of different compounds results in emission of light having a wavelength which is characteristic to the chemicals present in the fluids. The emissions are preferably detected by electro-optic unit 54.

Unit 54 preferably comprises several narrow band pass filters 58, one or more for each characteristic emission wavelength. A typical bandwidth of filters 58 is about 2 nm. Filters 58 are preferably mounted on a rotating wheel 61, positioned between the chamber 52 and a photodiode 62. When emission photons passing through filters 58 impinge on photodiode 62, an electric signal which is proportional to the number of photons is generated. For each filter, the intensity of the electric signal is used for determining presence or concentration of the respective chemical.

For example, in the case of chemical warfare agents, combustion of organo-phosphorus compounds yields POH* groups, while combustion of sulfur compounds yields $S_2$*. Four filters are preferably used in this case. Two filters are used for the measurement of POH* emission and two filters are used for the measurement of $S_2$* emission. The concentration of the chemical warfare agents is determined from the ratio between the emission intensity at the peak to the emission intensity at the minimum. In the present example, the peaks are located at wavelengths of 526 nm for phosphorus and 405.2 nm for sulfur and the minima are located at wavelengths of 518 nm for phosphorus and 411.5 nm for sulfur. The use of four different filters allows a simultaneous detection of sulfur and phosphorus compounds. In addition, the four filters can be used to determine existence of other chemicals, which may be present in the air during wartime, by analyzing spectral interferences arising thereby [S. M. Somani "Chemical Warfare Agents," Academic press Inc., 1992].

According to a preferred embodiment of the present invention, when feeding device 10 feeds detector 12 with enriched fluid sample 22, the detection sensitivity of detector 12 is increased at least by a factor of 10, more preferably at least by a factor of 30, most preferably at least by a factor of 50.

As stated, the sensitivity enhancement of chemical detector 12 is achieved by sorbing the target chemical from a large volume of fluid and desorbing it into a smaller volume. Commercially available chemical detectors typically use only a fraction (about 10%) of the incoming fluids for detection, whereby the other portion (about 90%) is used for other functions. For example, in flame photometric detectors, a portion of the incoming fluid is used for flame makeup.

While conceiving the present invention it has been realized that the detection sensitivity can be further increased by allowing enriched fluid sample 22 to enter directly into sensing element 26 of detector 12.

Reference is now made to FIG. 3c, which further details, in a schematic fashion, sensing element 26 and loose connector 24. Hence, according to a preferred embodiment of the present invention, loose connector 24 is positioned in close proximity (e.g., at an inlet 27) to sensing element 26. Preferably, to facilitate the loose connection between device 10 and detector 12, loose connector 24 is designed and constructed so as to allow environmental fluids 20 to bypass loose connector 24 and enter chamber 52 at all times. This can be achieved, for example, by providing a loose connector having a diameter which is different (i.e., smaller or larger) than the diameter of sensing element 26, so that environmental fluids 20 enter detector 12 through an opening 28 or gap formed between loose connector 24 and sensing element 26.

Figure 3D:
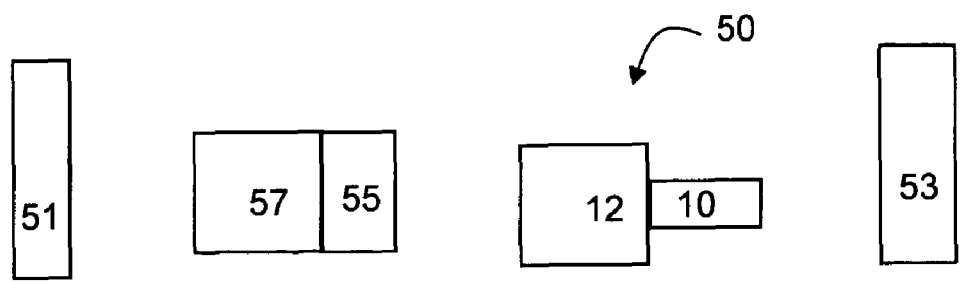
FIG. 3d is a simplified illustration of an air purifying system, according to a preferred embodiment of the present invention.

Reference is now made to FIG. 3d, which is a simplified illustration of an air purification system 60, which incorporates system 50. Hence, according to a preferred embodiment of the present invention system 60 comprises an inlet 51 and an outlet 53, whereby system 50, including detector 12 and device 10, is positioned therebetween. System 60 further comprises at least one purifying element 55 for purifying at least a portion of air entering inlet 51, thereby providing purified air. Any purifying element 55 can be used, including, without limitation a sorbent material, a radiation generator, particulate immobilizing medium and the like.

Additionally, system 60 may further comprise an airflow mechanism 57 for generating flow of the purified air through outlet 53. According to a preferred embodiment of the present invention detector 12 is capable of generating a signal indicative of the presence of at least one target chemical, in which case purifying element 55 is configured to receive the signal and initiate air purification. This embodiment is particularly useful when purifying element 55 is an active element, such as, but not limited to, a purifying element which is based on radiation, e.g., ultraviolet radiation.

Figure 4:
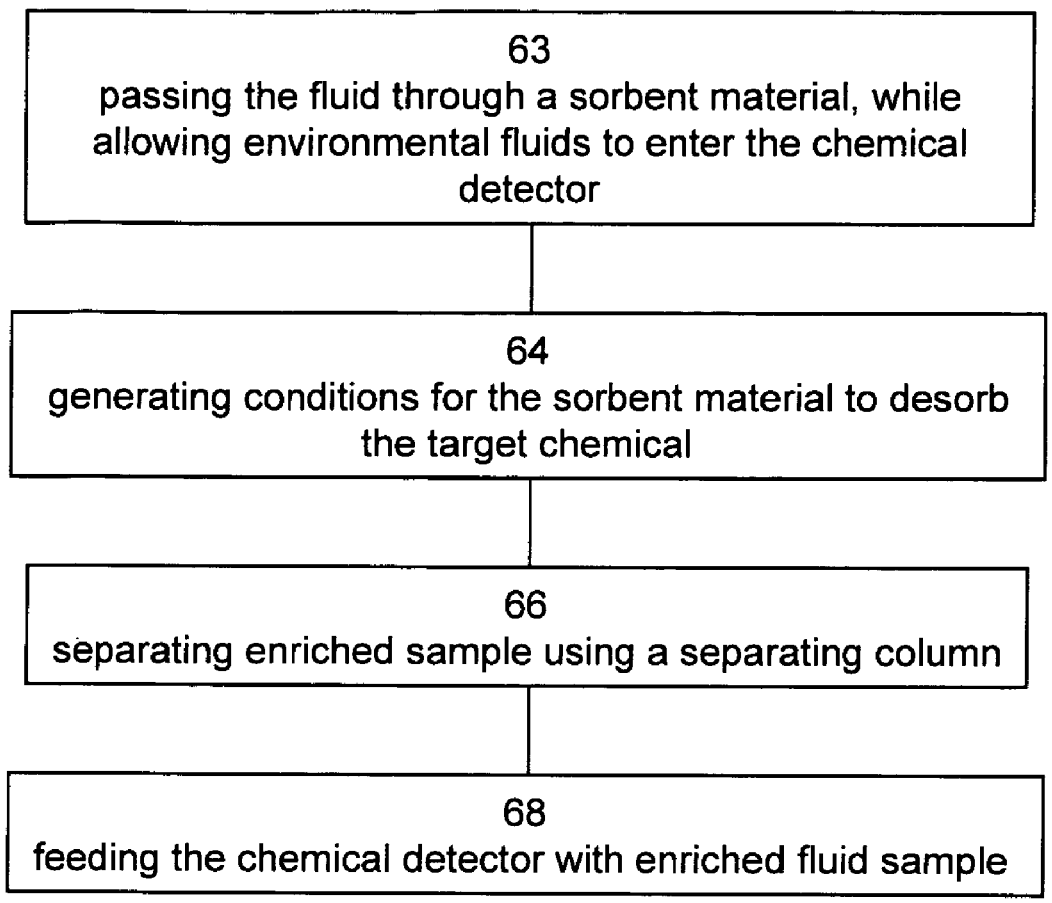
FIG. 4 is a flowchart diagram illustrating a method of improving detection sensitivity of a chemical detector, according to a preferred embodiment of the present invention.

According to an additional aspect of the present invention there is provided a method of improving detection sensitivity of a chemical detector. The method comprises the following method steps which are illustrated in the flowchart of FIG. 4. Selected steps of the method can be executed by device 10 or any other suitable device.

Hence, referring to FIG. 4, in a first step, designated by Block 63, environmental fluids 20 are passed through sorbent material 16, while allowing environmental fluids 20 to enter chemical detector 12, as further detailed hereinabove. In a second step of the method, designated by Block 64, conditions for sorbent material to desorb the target chemical are generated, as further detailed hereinabove. In an optional step, designated by block 66, the target chemicals are separated, e.g., using separating column 30, and in a forth step, designated by Block 68, detector 12 is fed with enriched fluid sample 22, as further detailed hereinabove.

The method, device and systems of the present invention can be used to detect or identify many target chemicals, including without limitation chemical warfare agents, toxic industrial chemical, explosives and a narcotic chemicals.

Specifically to chemical warfare agents, the following agents are contemplated: nerve blocking agents (e.g., tabun, methylphosphonothioic acid, sarin and soman), blister inducing agents (e.g., sulphur mustard, nitrogen mustard, distilled mustard, mustard lewisite, lewisite, phosgene oximine, ethyldichloroarsine and methyldichloroarsine), choke inducing agents (e.g., phosgene, diphosgene, chlorine and chloropicrin), vomiting inducing agents (e.g., diphenyl-dichloroarsine, adamsite and diphenylcyanoarsine) blood destructing agents (e.g., hydrogen cyanide, cyanogen chloride and arsine) and other chemical warfare agents.

It is expected that during the life of this patent many relevant chemical detectors will be developed, independently of in conjunction with new relevant chemicals and the scope of the terms "chemical detector" and "target chemical" is intended to include all such new technologies and materials a priori.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE

Reference is now made to the following example, which together with the above descriptions illustrates the invention in a non limiting fashion.

Using a Prototype Feeding Device for Improving Detection Sensitivity of Chemical Warfare Agents Materials and Methods Triethylphosphate (TEP from BDH, 99.5% purity), tributylphosphate (TBP from Fischer analytical) and parathion (from Supelco/chemservice, 97% purity) were used without further purification. Bis (2-chloroethyl) sulfide (sulfur mustard HD), O-Ethyl S-2-diisopropylaminoethyl methyl phosphonothiolate (VX) and O-isopropyl methyl phosphonofluoridate (sarin, GB) were synthesized at purity levels higher than 95% as measured by nuclear magnetic resonance.

Vapor generation was performed by bubbling dry nitrogen through 2-5 gr of liquid target chemical at a fixed temperature. The saturated nitrogen/target chemical mixture was diluted with air (1:10000) at 25° C. prior to detection by the feeding device of the present invention.

Figure 5:
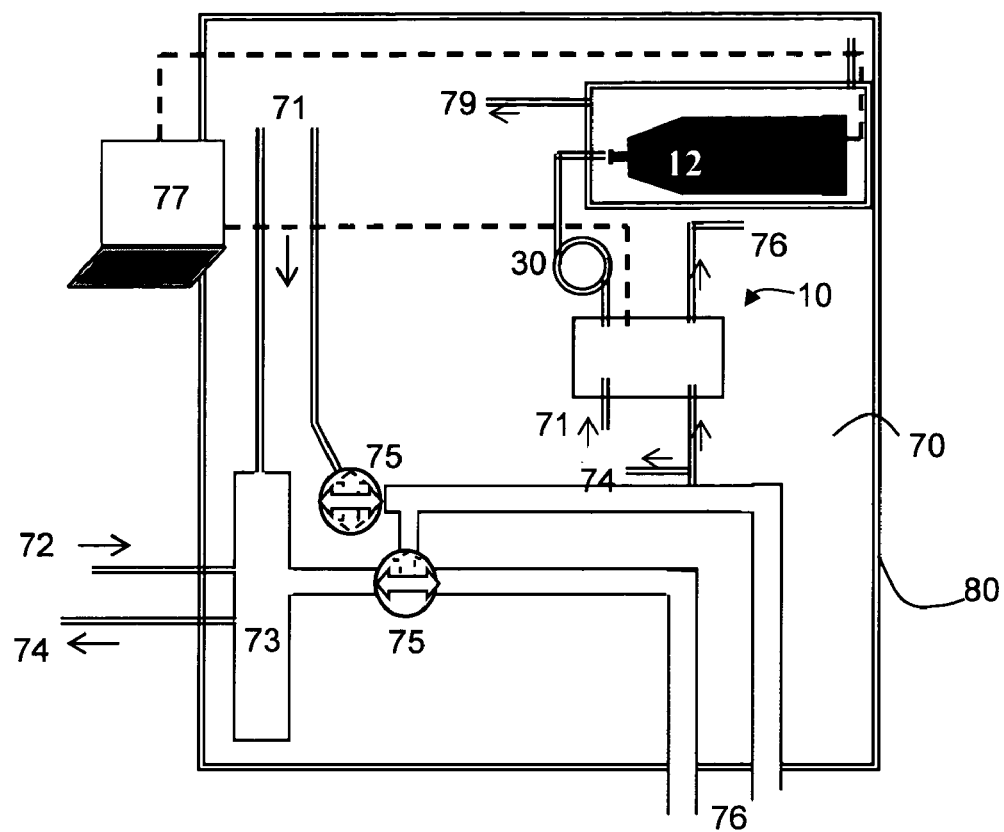
FIG. 5 is a schematic illustration of the experimental setup, designed for a prototype feeding device, according to a preferred embodiment of the present invention.

FIG. 5 is a schematic illustration of the experimental setup. Feeding device 10 with separating column 30 were placed inside a climatic chamber 70 located inside a chemical hood 80. Also shown in FIG. 5 are clean air entrances 71, chemical warfare agent entrance 72, a mixing chamber 73, sampling ports 74, three-way valves 75 for selecting between clean air and mixture of air and chemical warfare agents, vacuum channels 76 and a data processor 77. An additional port, designated 79, was assigned for pumping out gas for safety reasons.

Device 10 was controlled by data processor 77. The sorption and desorption duration, as well as the heating parameters for the sorbent element and separating column were determined during the experiment.

Target chemical concentrations in air stream were determined by bubbling a known volume of contaminated air through hexane or iso-octane (Analytical from Aldrich) and injecting the solution to a GC/FPD (Agilent 6890). The GC/FPD was calibrated by injecting standard solutions. Chemical warfare agent byproducts and degradation products were identified by injecting the same sample to a quadruple GC/MS (agilent 6890/5973N).

Detector 12 was an AP2C detector, (Proengin, France) which is based on FPD technology. The AP2C pumps about 1.2 liter of air per minute. Most of the pumped air (85-95%) is used for flashing the detectors optics ("make-up") while the other portion about 5-15% is delivered to the combustion chamber.

In accordance with a preferred embodiment of the present invention, the loose connection between detector 12 and feeding device 10 was design to deliver the enriched fluid sample air directly into the combustion chamber, allowing detector 12 to pump the make-up air from the environment. The combustion chamber inlet (1.1 mm in diameter) was placed inside the outlet of the separating column (2 mm in diameter). It was verified that the delivery of the enriched fluid sample to the combustion chamber did not affect the normal operation of detectors 12. For example, no occurrences of flame choking were recorded.

The experiment included four major phases: (i) sorption of the chemical warfare agents in the sorbent material; (ii) desorption of the chemical warfare agents out of the sorbent material and into the separating column; (iii) separation of the enriched fluid sample in the separating column; and (iv) detection of the chemical warfare agent by the AP2C detector.

Figure 6:
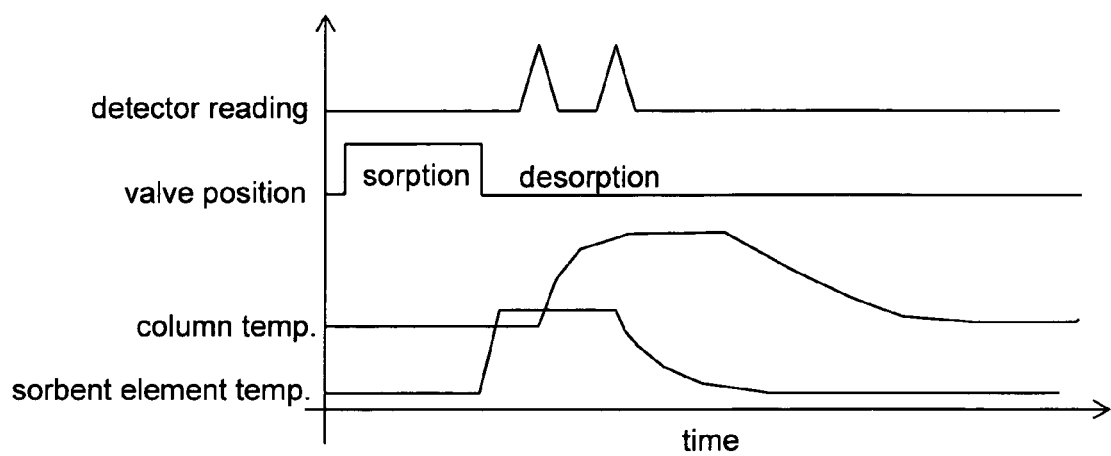
FIG. 6 show temperatures of the sorbent element and the separating column, valve position and detector reading as a function of time for a four-phase cycle of an experiment performed using the experimental setup of FIG. 5.

FIG. 6 show the temperatures of the sorbent element and the separating column, the valve position and the detector reading as a function of time for a four-phase cycle of the experiment.

Table 1 below summarizes the operational parameters used in the experiment.

TABLE 1

| Process | Parameter | Value |
|---|---|---|
| Sampling | Sampling time, seconds | 15-1200 |
| | Sample flow rate, cm$^3$/minute | 100-1000 |
| | sorbent element temperature, ° C. | 50 |
| Desorption | sorbent element heat time, seconds | 60 |
| | Desorption temperature, ° C. | 270 |
| Separation | Hold time, seconds | 65 |
| | Column heat rate at 100° C., ° C./min* | 125 |
| | Column final temperature, ° C. | 130 |
| | Carrier flow rate, cm$^3$/minute** | 100-150 |

*For VX heating the rate was 330
**Constant flow

Results and Discussion

Selectivity

The feeding device of the present invention was challenged with several chemical warfare agents, parathion and OP compounds. Each compound eluted at a different time from the column and recorded by the detector. The identification of target chemicals was based on the elution time, and detection channels (phosphorus detection channel and sulfur detection channel).

FIGS. 7a-e show chromatograms obtained for TEP, TBP, parathion, GB, HD and VX using the feeding device of the present invention was. The noise level in many cases is zero since the AP2C output is digital and signal fluctuation are truncated by the detector during digitization. For HD, GB, TEP and TBP a single peak was observed.

Parathion gave rise to three peaks in the phosphorus detection channel. The first peak was assigned to parathion degradation products; the second peak to TBP arising from previous contamination of the experimental system ($5 \times 10^{-4}$ µg/L of TBP were observed by off-line GC/FPD analysis), and the third peak to parathion.

When VX vapor in air was sampled, two peaks in the phosphorus detection channel and two in the sulfur detection channel were observed. Assignment of this peak was performed by sampling the contaminated air to iso-octane and injecting a portion of the liquid sample to a quadruple GC/MS. The first peak in the phosphorus detection channel was assigned to O, S-diethyl methyl phosphonothioate (DEMPT) which is a byproduct of VX [N. B. Munro, S. S. Talmage, Guy D. Griffin, L. C. Waters, A. P. Watson, J. F. King, and V. Hauschild, Envi. Health Persp., 107, 933-973 (1999)] and the second to VX. The first peak in the sulfur detection channel was assigned mainly to 2-(Bis diisopropylamino) ethanethiol (BDT), and the second to 2-diisopropyl aminoethyl ethyldisulfide (DIS). Both DIS and BDT are known to be degradation products of VX [N. B. Munro et al., supra].

Figures 7A, 7B, 7C, 7D, 7E:
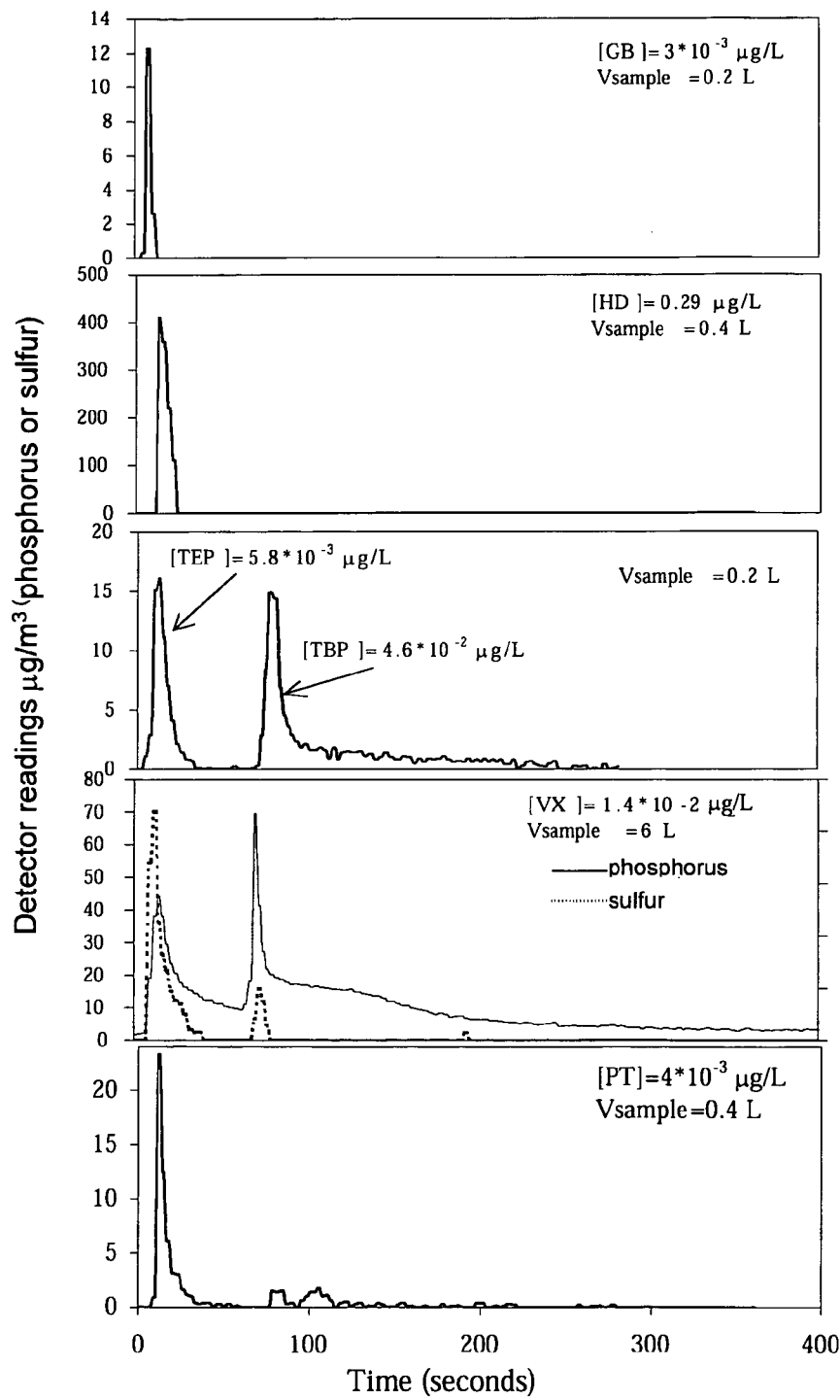
FIGS. 7a-e show chromatograms obtained for trace levels of TEP, TBP, parathion, GB, HD and VX vapor in air, obtained using the feeding device of the present invention.

Since the sensitivity in the sulfur detection channel is about 100 lower than in the phosphorus detection channel, detection of DIS in the sulfur detection channel can be done by sampling a larger amount of these target chemicals (see FIG. 7d). VX and parathion byproducts were identified by an off-line analysis of a fraction from the contaminated air which was not passing through the feeding device. Therefore, the source for those materials is not due to the operation of the feeding device, but rather impurities in the original sample. It is clear from the chromatogram shown above that the feeding device can separate between VX and DEMPT, but when VX concentration is low, it may be masked by the tail of the DEMPT chromatographic peak. Peak masking can be partially avoided by increasing the sorbent element temperature when sampling the air. In this way, the amount of DEMPT trapped on the sorbent material is decreased, with minimal effect on VX trapping efficiency.

Figures 8A, 8B, 8C:
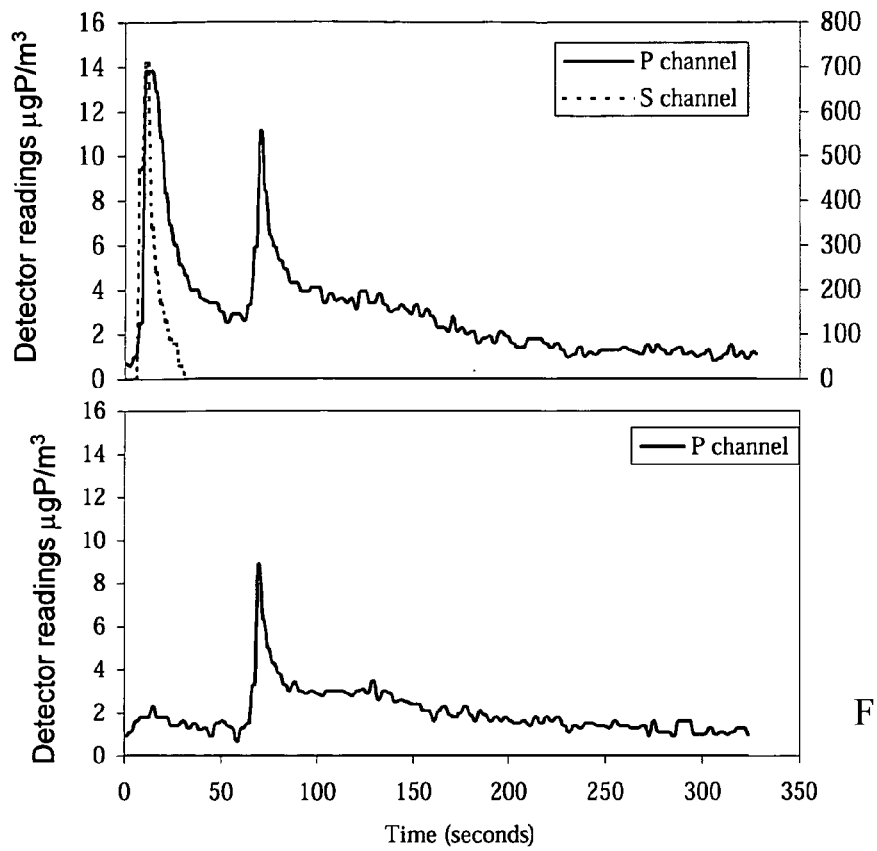
FIGS. 8a-b show chromatograms obtained for sampling air contaminated with 0.01 μg/L of VX vapor in air, at a temperature of 50° C.
FIG. 8c shows the relative peaks amplitudes of VX, DEMPT and BDT as a function of the temperature of the sorbent material.

FIGS. 8a-b show chromatograms obtained for sampling 0.01 µg/L of air contaminated with VX at sorbent element temperatures of 50° C. (FIGS. 8a) and 150° C. (FIG. 8b). FIG. 8c shows the relative peaks amplitudes of VX, DEMPT and BDT as a function of the sorbent material temperature during the sorption phase.

As shown in FIGS. 8a-c the trapping efficiency of DEMPT and BDT is reduced when elevating the sorbent element temperature during the sorption phase. By reducing the trapping efficiency of DEMPT, masking of VX is reduced and the selectivity of the feeding device of the present invention is improved.

Sensitivity

The minimal detection limits were evaluated by measuring the signal to noise ratio (SNR) at a known chemical warfare agent concentration and extrapolating to SNR=3, assuming the detector response is linear [Kendler, S. Zaltsman, A. Frishman, G. Instrum. Sci. Technol. 31, 357 (2003)].

It was found that the minimal detection limits is $1.5 \times 10^{-5}$ μg/L for GB and $3.2 \times 10^{-4}$ μg/L for VX. The difference between VX and GB is mainly due to the fact that GB is 1000 more volatile than VX. Thus, GB is transferred from the sorbent element to the column faster, hence experiences a lesser dilution.

Table 2 below summarizes the minimal detection limits evaluated in the present experiment.

TABLE 2

| Target chemical | Elution time (seconds) | Standard Deviation (seconds) | FWHM (seconds) | Elution temperature (° C.) | BP$^{(i)}$ (° C.) | Detection limit (μg/L air) |
|---|---|---|---|---|---|---|
| GB | 8.4 | 0.9 | 6 | 50 | 147 | $1.5 \times 10^{-5}$ |
| TEP | 16 | 2.3 | 12 | 50 | 215 | $4 \times 10^{-5}$ |
| HD | 14 | 1.1 | 8 | 50 | 227.8 | 0.025 |
| TBP | 80 | 1.4 | 8 | 86 | 289 | $1.8 \times 10^{-4}$ |
| VX$^{(ii)*}$ | 69 | 1.5 | 17 | 135 | 300 | $3 \times 10^{-4}$ |
| VX$^{(ii)**}$ | 87 | | 19 | 106 | 300 | $5 \times 10^{-4}$ |
| DEMPT$^{(iii)}$ | 14 | 1.1 | 10 | 50 | | — |
| BDT$^{(iii)}$ | 11 | 1.5 | 6 | 50 | | — |
| parathion | 99 | 4.2 | 8 | 118 | 375 | $2.4 \times 10^{-4}$ |
| | 11 | 1.4 | 6 | 50 | | |

Remarks:
$^{(i)}$Boiling points were taken from S. M. Somani "Chemical Warfare Agents," Academic press Inc. 1992, parathion and TBP boiling points from "Niosh pocket guide to chemical hazards" http://www.cdc.gov/niosh/npg;
$^{(ii)}$For VX two heating rates were compared, 330 (*) and 125 (**) degrees per minute. For all other compounds colunm heat rate was always 125° C./minute at 100° C.
$^{(iii)}$DEMPT is VX byproduct BDT is a volatile degradation product of VX It will be appreciated that the minimal detection limits can be different from the practical quantitation limit (PQL). For example, for VX, the PQL can be 3-5 times higher than the minimal detection limits, mainly due to peak tailing and masking by DEMPT, while for GB the difference between minimal detection limits and PQL is lower.

The minimal detection limits listed in Table 2 are calculated for sampling one liter of contaminated air. One of ordinary skill in the art will appreciate that higher sensitivity can be obtained by increasing the sorption time so as to accumulate higher quantities of target chemicals in the sorbent material. In any event, according to a preferred embodiment of the present invention the sorption time is selected such that the volume of the fluid sample is smaller than the characteristic breakthrough volume of the target chemicals, so as to maintain a linear relationship between the signal intensity and volume of the sample.

Figure 9A:
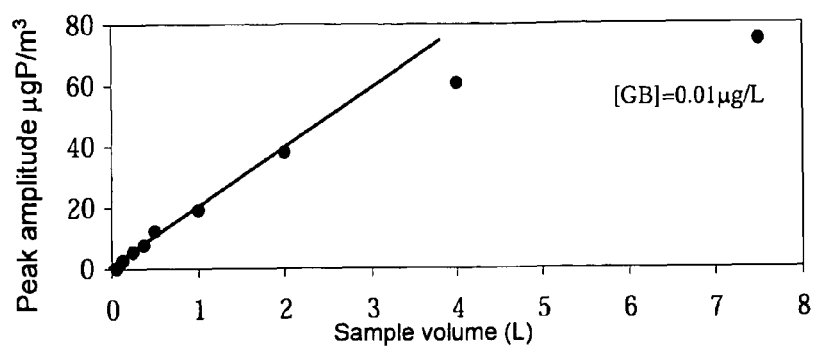
FIGS. 9a-c show the relationship between the signal intensity and the sample volume for GB (FIG. 9a), VX, DEMPT, BDT (FIG. 9b) and HD (FIG. 9c), obtained in the second operational phase of the feeding device, according to a preferred embodiment of the present invention.
Figure 9B:
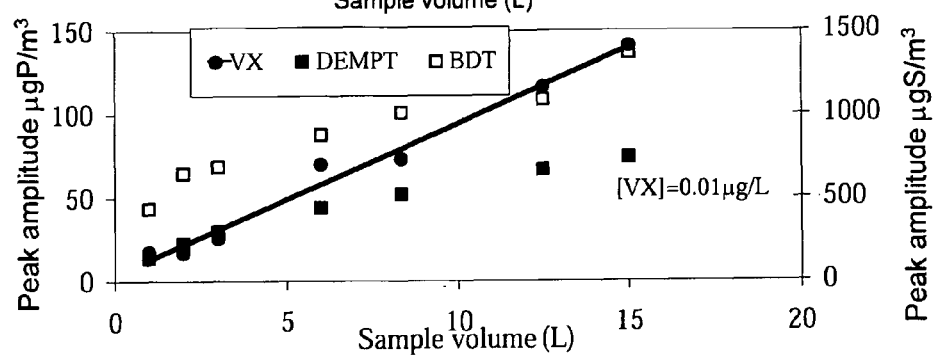
Figure 9C:
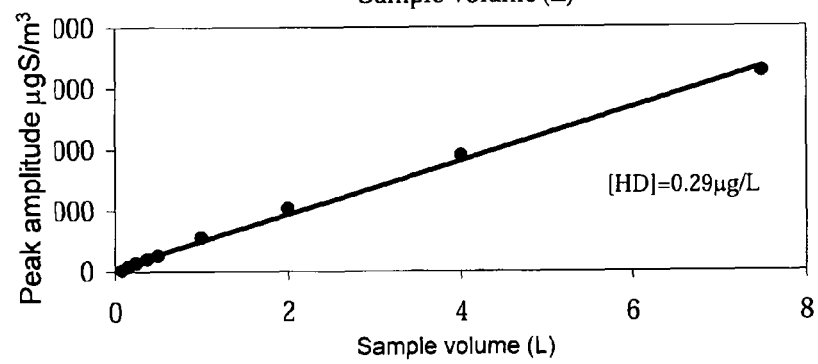

FIGS. 9a-c show the relationship between the signal intensity and the sample volume for GB (FIG. 9a), VX, DEMPT, BDT (FIG. 9b) and HD (FIG. 9c). As shown the breakthrough volume for GB is about 2-4 liters. No breakthroughs were observed for VX up to sample volume of 15 liters and for HD up to sample volume of 8 liters. Thus, by increasing the sample volume the minimal detection limits show in Table 2 can be improved by a factor of 5 for GB and by a factor of at least 10 VX and HD. Since DEMPT is more volatile than VX, part of it is not trapped in the sorbent material, when a large volume of air is sampled. As a result, masking of the VX peak by the DEMPT tail is reduced by increasing the sample volume. This effect can be used for further improving both the PQL and the minimal detection limits of VX.

Optimization

The choice of fluid flow rate used for desorption and separation of the target chemicals is affected by several factors: increasing air flow rate prompts desorption of the target chemicals from the sorbent material, giving rise to sharp pronounced chromatographic peaks, shortened analysis time and reduced elution temperature. On the other hand, if the flow rate exceeds the detector's flow rate, a fraction of the air can be lost through the loose connector and may not arrive to the sensing element of the detector.

Reducing peak width may increase sensitivity as long as peak width is higher than the detector digitization time, which is typically about 2 seconds, while the intensity of very sharp peaks may be underestimated.

Another issue that has to be taken into account is the effect of fluid linear velocity on chromatographic performance. At high fluid velocity, the number of theoretical plates is lowered and chromatographic separation is degraded.

Figure 10:
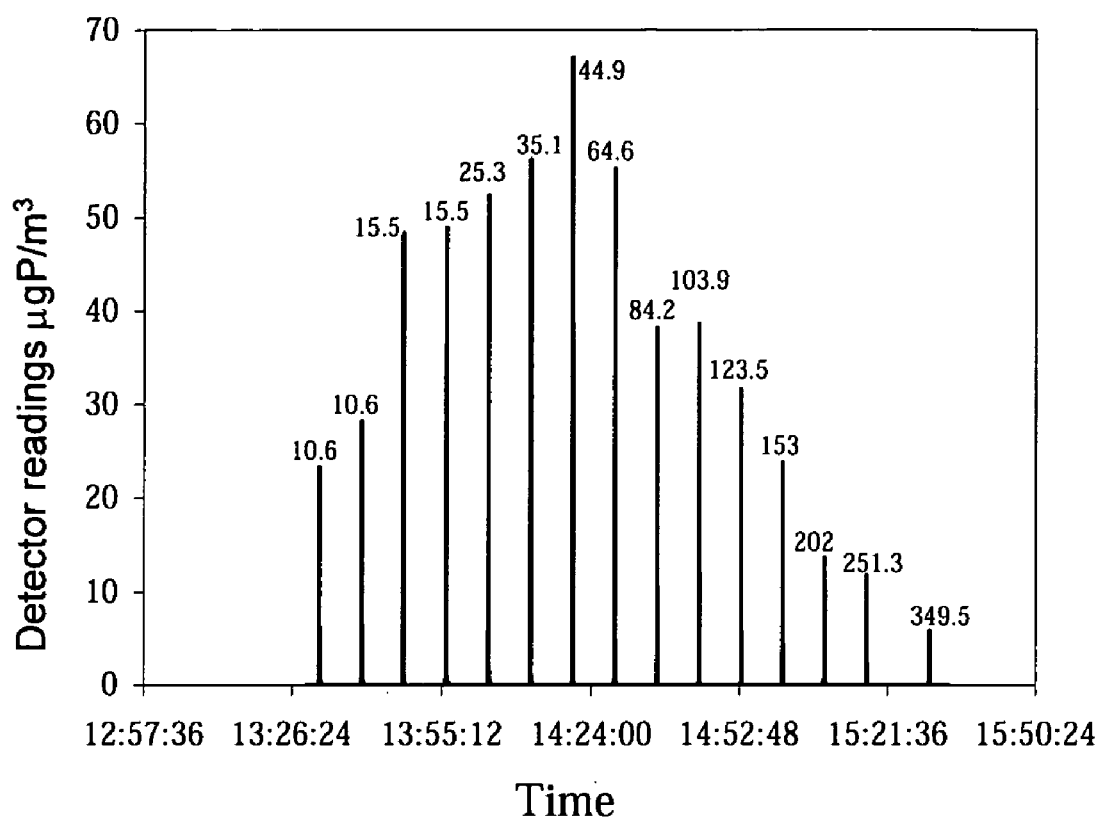
FIG. 10 shows chromatograms obtained for GB vapor using several flow rates, according to a preferred embodiment of the present invention.

FIG. 10 shows chromatograms obtained for GB vapor using several fluid flow rates. At flow rate of 45 ml/minute, the minimal detection limits for GB is three times higher than for 150 ml/minute.

Figures 11A, 11B, 11C:
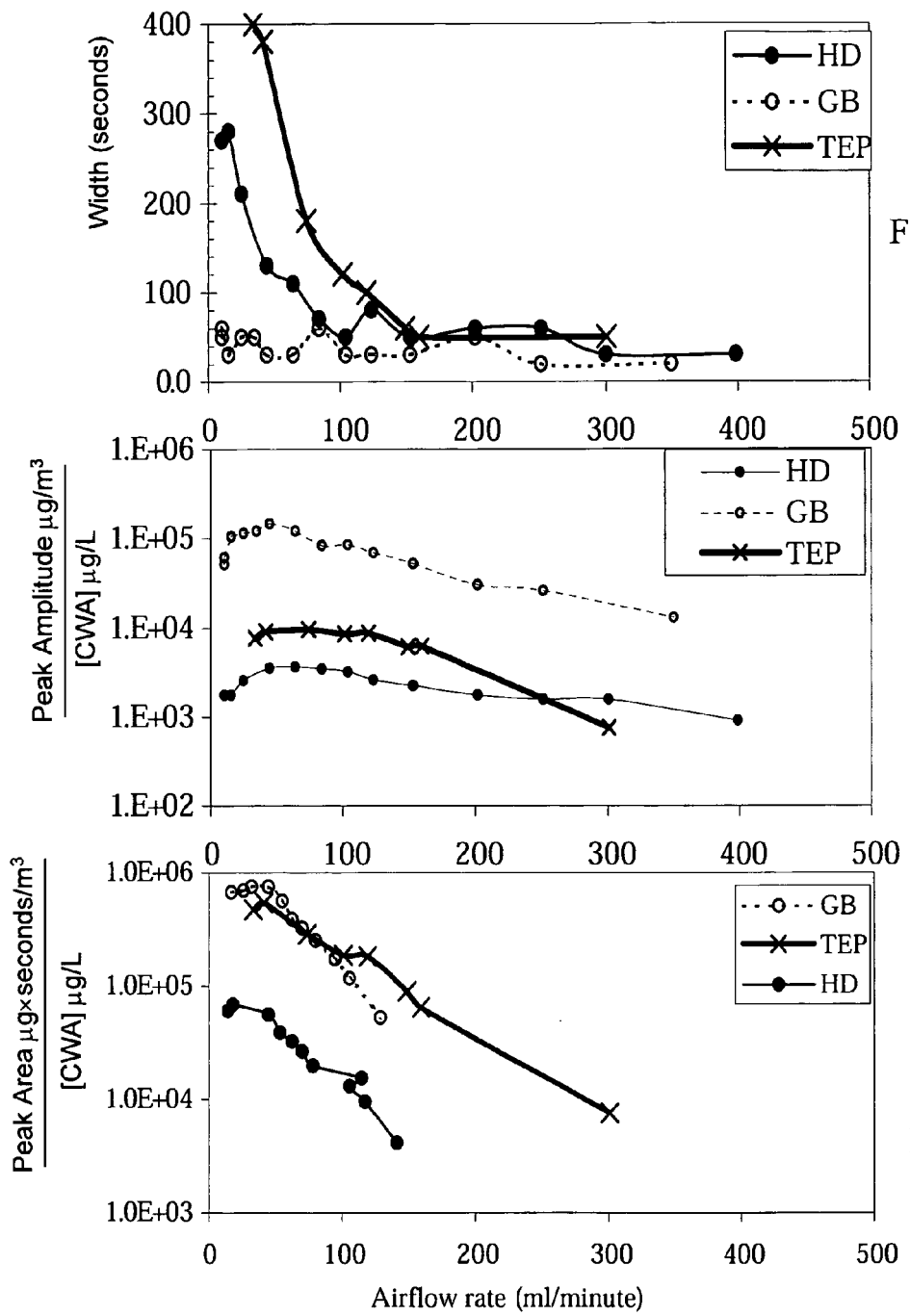
FIGS. 11a-c show the effect of flow rate on peak widths (FIG. 11a), amplitude (FIG. 11b) and area (FIG. 11c) for GB, TEP, and HD, according to a preferred embodiment of the present invention.

FIGS. 11a-c show the effect of flow rate on the widths (FIG. 11a), amplitude (FIG. 11b) and area (FIG. 11c) of the peaks for GB, TEP, and HD. The amplitude and area are normalized by the concentrations of the chemical warfare agents. As shown in FIGS. 11a-c, by increasing the flow rate, the chromatographic peaks for all target chemicals become narrower. For GB a peak width at the same order of magnitude as the AP2C digitization time was observed, implying underestimating of the sensitivity for GB at these conditions. For TEP and HD, which are less volatile compounds than GB, the peak widths are above than five seconds.

With respect to the peak amplitudes, for GB the maximum amplitude is obtained at a flow rate of 45 ml/minute while for HD and TEP maximum peak amplitude is obtained at a flow rate of 80-120 ml/minute.

The effect of flow rate on peak area is very similar for all the tested target chemicals. A maximal area is obtained when the flow rate is 30-50 ml/minute, whereas above this rate, part of the sample is lost. The resemblance between TEP and GB suggests that desorption process of these compounds is very efficient, and does not involve degradation of the target chemicals during thermal desorption in air.

Figures 12A, 12B, 12C:
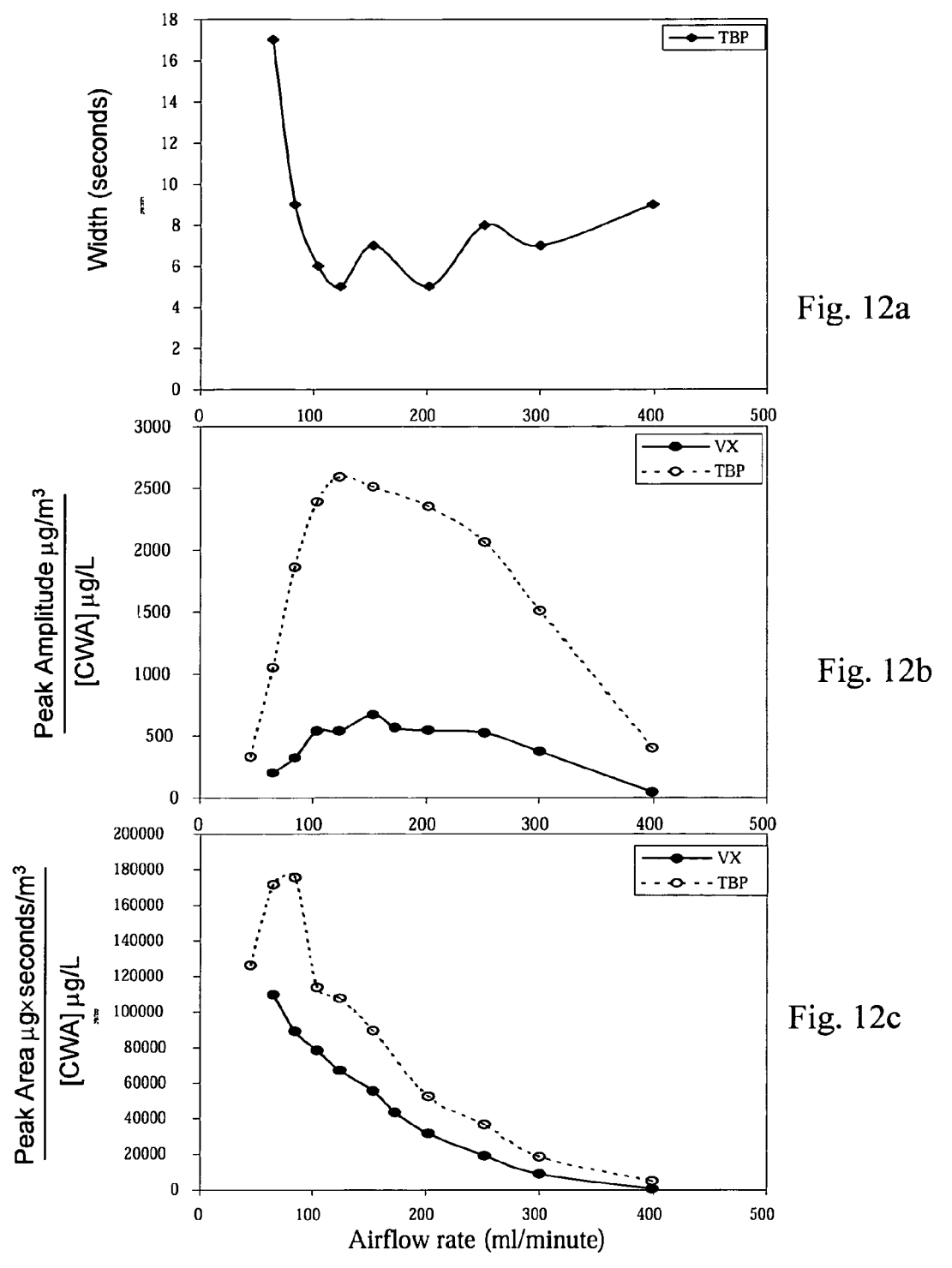

FIG. 12a shows the effect of flow rate on the width of the peaks for TBP, and FIGS. 12b-c show the effect of flow rate on the amplitude (FIG. 12b) and area (FIG. 12c) of the peaks for TBP and VX. The width for VX was not obtained due to its long tail (see FIG. 7d).

For TBP the peak width is reduced when the flow rate is increased to 150-200 ml/minute. Above 200 ml/minute, the peak width is increased, implying a reduction of focusing efficiency in the column at high flow rates.

The peak amplitude for TBP is four times higher than for VX. This difference may be assigned either to degradation of VX during heating of the sorbent element, resulting a non-volatile, product, hence undetectable by thermal desorption, or due to the tailing of the chromatographic peak.

The observed peak area of VX is only about 50% lower than for TBP, because the estimation of area of tailed peaks involves a significant error. It is therefore concluded that VX desorption is slow, resulting in low and tailed chromatographic peaks, but does not involve substantial decomposition.

Hence, according to a preferred embodiment of the present invention the following consideration can be made when selecting the flow rate.

If the target chemical's volatility is known, the operator can choose an optimal flow rate depending on the target chemical. For example, about 50 ml/minute for a volatile target chemical like GB and about 150 ml/minute for less volatile target chemicals like VX or parathion.

On the other hand, if the chemical's volatility is not known, the operator can choose high flow rates, about 150 ml/minute, thereby compromising the sensitivity for volatile target chemicals (e.g., GB) while having good sensitivity and selectivity for less volatile target chemicals VX.

Figure 13A:
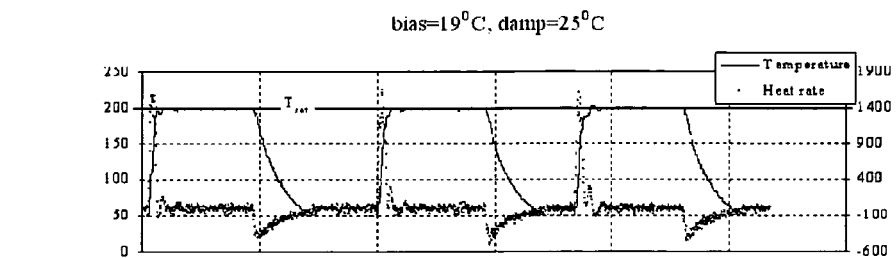
FIGS. 13a-d show heating profiles of the sorbent element using several different biasing and damping parameters, according to a preferred embodiment of the present invention.
Figure 13B:
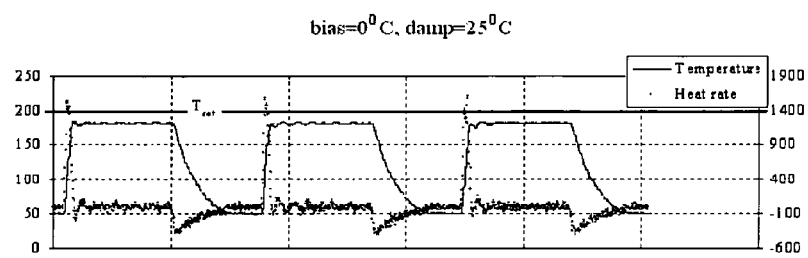
Figure 13C:
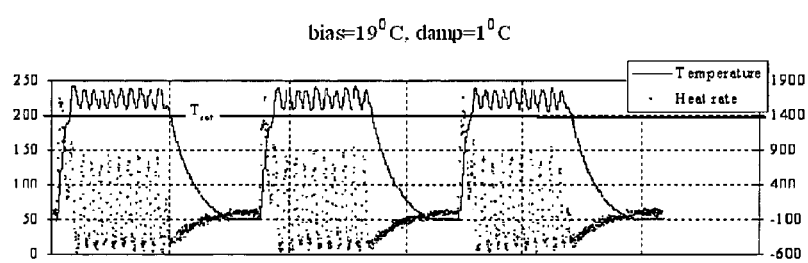
Figure 13D:
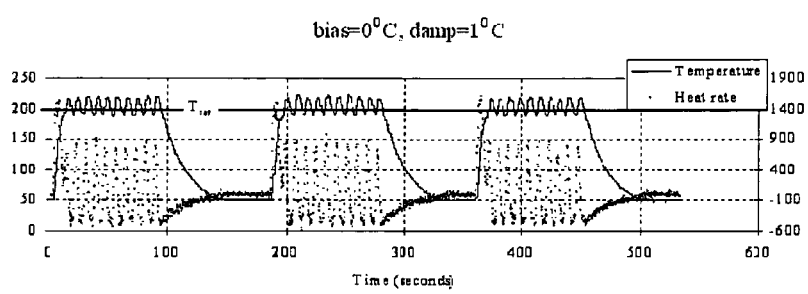

FIGS. 13a-d show the heating profile of the sorbent element, when heated from 50° C. to 200° C., using different biasing and damping parameters (see Equation 1 hereinabove). Specifically, FIG. 13a show heating profile for B=19° C. and D=25° C., FIG. 13b show heating profile for B=0° C. and D=25° C., FIG. 13c show heating profile for B=19° C. and D=1° C., and FIG. 13d show heating profile for B=0° C. and D=1° C., As shown in FIGS. 13a-d, the optimal set of parameters is in the case shown in FIG. 13a (B=19° C. and D=25° C.), where a heating rate of 1600° C. per minute was obtained. As these parameters depend on the thermal mass of the sorbent element, the optimal values of B and D are preferably determined once the type and conditions of the sorbent element are known.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of improving detection sensitivity of a chemical detector, the method comprising:
    (a) passing a fluid sample potentially having at least one target chemical through a sorbent material, thereby sorbing said at least one target chemical in said sorbent material;
    (b) generating conditions for said sorbent material to desorb said at least one target chemical of said sorbent material, thereby providing an enriched fluid sample; and
    (c) feeding the chemical detector with said enriched fluid sample;
    wherein said steps (a)-(c) are executed while allowing environmental fluids containing said at least one target chemical to enter the chemical detector and be detected thereby for existence of said at least one target chemical at all times, and
    wherein the environmental fluids that enters during said desorption, the environmental fluids that enters during said sorption and the environmental fluids in the environment contain similar concentrations of said at least one target chemical;
    thereby improving the detection sensitivity of the chemical detector.

2. The method of claim 1, further comprising separating said enriched sample using a separating column.

3. The method of claim 1, wherein said enriched fluid sample is fed to a sensing element of the chemical detector.

4. The method of claim 1, wherein said sorbent material is hydrophobic.

5. The method of claim 4, wherein a water vapor breakthrough volume through said sorbent material is smaller than a breakthrough volume of said at least one target chemical through said sorbent material by at least two orders of magnitude.

6. The method of claim 1, wherein said generation of conditions for said sorbent material to desorb said at least one target chemical is by heating using a heating element.

7. The method of claim 6, wherein said heating is to a predetermined temperature, said predetermined temperature being sufficiently below a decomposing temperature of said at least one target chemical.

8. The method of claim 6, wherein said heating is at a predetermined heating rate, said predetermined heating rate being sufficiently fast so as to prevent or minimize decomposition of said at least one target chemical.

9. The method of claim 1, wherein said sorbent material is absorbent material.

10. The method of claim 1, wherein said sorbent material is adsorbent material.

11. The method of claim 1, wherein said sorbent material is selected from the group consisting of porous inert hydrophobic polymer, activated non-synthetic carbon, activated synthetic carbon, silica, alumina and combinations thereof.

12. The method of claim 1, wherein said sorbent material comprises a solid support.

13. The method of claim 1, wherein said at least one target chemical is selected from the group consisting of a chemical warfare agent, a toxic industrial chemical, an explosive and a narcotic chemical.

14. The method of claim 1, wherein the chemical detector is a portable chemical detector.

15. The method of claim 1, wherein said sorbent material desorbs said at least one target chemical only into air without using a supply pure gas for carrying said at least one target chemical, thereby providing an enriched air sample.

16. The method of claim 1, further comprising temporarily connecting a feeding device having said sorbent material to the chemical detector.

* * * * *